United States Patent
Torres et al.

(10) Patent No.: US 11,951,331 B2
(45) Date of Patent: Apr. 9, 2024

(54) MAGNETIC RESONANCE SIGNATURE MATCHING (MRSIGMA) FOR REAL-TIME VOLUMETRIC MOTION TRACKING AND ADAPTIVE RADIOTHERAPY

(71) Applicant: Memorial Sloan Kettering Cancer Center, New York, NY (US)

(72) Inventors: Jose Ricardo Otazo Torres, New York, NY (US); Li Feng, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 347 days.

(21) Appl. No.: 17/605,394

(22) PCT Filed: Apr. 24, 2020

(86) PCT No.: PCT/US2020/029724
§ 371 (c)(1),
(2) Date: Oct. 21, 2021

(87) PCT Pub. No.: WO2020/219814
PCT Pub. Date: Oct. 29, 2020

(65) Prior Publication Data
US 2022/0203132 A1 Jun. 30, 2022

Related U.S. Application Data

(60) Provisional application No. 62/838,922, filed on Apr. 25, 2019.

(51) Int. Cl.
*A61N 5/10* (2006.01)
*G01R 33/48* (2006.01)
(Continued)

(52) U.S. Cl.
CPC ......... *A61N 5/1049* (2013.01); *A61N 5/1067* (2013.01); *G01R 33/4826* (2013.01);
(Continued)

(58) Field of Classification Search
CPC ................ A61N 5/1049; A61N 5/1067; A61N 2005/1055; G06T 7/28; G06T 2207/10088;
(Continued)

(56) References Cited

U.S. PATENT DOCUMENTS 8,634,898 B2 * 1/2014 Adler .................. A61N 5/1049
600/428
9,940,713 B1 * 4/2018 Bhat ......................... G06T 7/70
(Continued)

OTHER PUBLICATIONS

Bjerre T, Crijns S, af Rosenschold PM, Aznar M, Specht L, Larsen R, Keall P. Three-dimensional MRI-linac intra-fraction guidance using multiple orthogonal cine-MRI planes. Phys Med Biol 2013;58(14):4943-4950.
(Continued)

*Primary Examiner* — Dixomara Vargas
(74) *Attorney, Agent, or Firm* — Foley & Lardner LLP

(57) ABSTRACT

Described is an approach for tracking 3D organ motion in real-time using magnetic resonance imaging (MRI). The approach may include offline learning, which may acquire signature and 3D imaging data over multiple respiratory cycles to create a database of high-resolution 3D motion states. The approach may further include online matching, which may acquire signature data only in real-time (latency less than 0.2 seconds). From a motion state and motion signature database, the 3D motion state whose signature best (or sufficiently) matches the newly-acquired signature data may be selected. Real-time 3D motion tracking may be accomplished by performing time-consuming acquisition and reconstruction work in an offline learning phase, leaving
(Continued)

just signature acquisition and correlation analysis in an online matching step, minimizing or otherwise reducing latency. The approach may be used to adapt radiotherapy procedures based on tumor motion using a magnetic resonance linear accelerator (MR-Linac) system.

20 Claims, 11 Drawing Sheets

(51) Int. Cl.
*G01R 33/56* (2006.01)
*G06T 7/246* (2017.01)
*G06V 20/64* (2022.01)
*G06V 40/20* (2022.01)

(52) U.S. Cl.
CPC .......... *G01R 33/5608* (2013.01); *G06T 7/248* (2017.01); *G06V 20/64* (2022.01); *G06V 40/20* (2022.01); *A61N 2005/1055* (2013.01); *G06T 2207/10088* (2013.01); *G06T 2207/20081* (2013.01); *G06T 2207/30241* (2013.01); *G06V 2201/031* (2022.01)

(58) Field of Classification Search
CPC  G06T 2207/20081; G06T 2207/30241; G06V 20/64; G06V 40/20; G06V 2201/031; G01R 33/4823; G01R 33/5608
See application file for complete search history.

(56) References Cited

U.S. PATENT DOCUMENTS

| | | | |
|---|---|---|---|
| 2005/0261570 | A1 | 11/2005 | Mate et al. |
| 2010/0113911 | A1 | 5/2010 | Dempsey |
| 2011/0044524 | A1 | 2/2011 | Wang et al. |
| 2011/0175609 | A1* | 7/2011 | Hu .................... G01R 33/3415 324/309 |
| 2011/0243401 | A1* | 10/2011 | Zabair ..................... G06T 7/33 382/128 |
| 2013/0030283 | A1 | 1/2013 | Vortman et al. |
| 2013/0188830 | A1 | 7/2013 | Ernst et al. |
| 2014/0213872 | A1 | 7/2014 | Rahman et al. |
| 2016/0128592 | A1 | 5/2016 | Rosen et al. |
| 2018/0268558 | A1* | 9/2018 | Bauer ..................... G06T 7/254 |
| 2019/0209867 | A1* | 7/2019 | Sun ....................... A61N 5/1039 |
| 2020/0337592 | A1* | 10/2020 | Brada ................. G01R 33/5608 |
| 2021/0118205 | A1* | 4/2021 | Huang ................. G01R 33/561 |
| 2022/0047227 | A1* | 2/2022 | Heukensfeldt Jansen .................... A61B 6/5205 |
| 2022/0338829 | A1* | 10/2022 | Giese ..................... G06T 7/277 |
| 2023/0377724 | A1* | 11/2023 | Vazquez Romaguera .................... G16H 30/40 |

OTHER PUBLICATIONS

Cervino L, Du J, Jiang SB. MRI-guided tumor tracking in lung cancer radiotherapy. Phys Med Biol. 2011; 56:3773-3785.

Chan RW, Ramsay EA, Cunningham CH, Plewes DB. Temporal Stability of Adaptive 3D Radial MRI Using Multidimensional Golden Means. Magnetic Resonance in Medicine 2009;61(2):354-363.

Chandarana H, Block TK, Rosenkrantz AB, Lim RP, Kim D, Mossa DJ, Babb JS, Kiefer B, Lee VS. Free-breathing radial 3D fat-suppressed TI-weighted gradient echo sequence: a viable alternative for contrast-enhanced liver imaging in patients unable to suspend respiration. Investigative radiology 2011;46(10):648-653.

Chandarana H, Wang H, Tijssen RHN, Das IJ. Emerging role of MRI in radiation therapy. Journal of magnetic resonance imaging: JMRI 2018;48(6):1468-1478.

Cheng JY, Zhang T, Ruangwattanapaisam N, Alley MT, Uecker M, Pauly JM, Lustig M, Vasanawala SS. Free-breathing pediatric MRI with nonrigid motion correction and acceleration. Journal of magnetic resonance imaging: JMRI 2015;42(2):407-420.

Dempsey J, Benoit D, Fitzsimmons J, Haghighat A, Li J, Low D, Mutic S, Palta J, Romeijn H and Sjoden G. A device for realtime 3D image-guided IMRT. Int J Radiat Oncol Biol Phys. 2005; 63(1):S202.

Deng Z, Pang J, Yang W, Yue Y, Sharif B, Tuli R, Li D, Fraass B, Fan Z. Four-dimensional MRI using three-dimensional radial sampling with respiratory self-gating to characterize temporal phase-resolved respiratory motion in the abdomen. Magnetic resonance in medicine 2016;75(4): 1574-1585.

Fayad H, Pan T, Pradier O, Visvikis D. Patient specific respiratory motion modeling using a 3D patient's external surface. Med Phys 2012;39(6):3386-3395.

Feng L, Axel L, Chandarana H, Block KT, Sodickson DK, Otazo R. XD-Grasp: Golden-angle radial MRI with reconstruction of extra motion-state dimensions using compressed sensing. Magn Reason Med 2016;75(2):775-788.

Feng L, Grimm R, Block KT, Chandarana H, Kim S, Xu J, Axel L, Sodickson DK, Otazo R. Golden-angle radial sparse parallel MRI: combination of compressed sensing, parallel imaging, and golden-angle radial sampling for fast and flexible dynamic volumetric MRI. Magn Reson Med 2014;72(3):707-717.

Feng L, Huang C, Shanbhogue K, Sodickson DK, Chandarana H, Otazo R. Racer-Grasp: Respiratory-weighted, aortic contrast enhancement-guided and coil-unstreaking golden-angle radial sparse MRI. Magnetic resonance in medicine 2018;80(1):77-89.

Feng L, Srichai MB, Lim RP, Harrison A, King W, Adluru G, Dibella EV, Sodickson DK, Otazo R, Kim D. Highly accelerated real-time cardiac cine MRI using k-t Sparse-Sense. Magn Reson Med. 2013;70(1):64-74.

Han F, Zhou Z, Du D, Gao Y, Rashid S, Cao M, Shaverdian N, Hegde JV, Steinberg M, Lee P, Raldow A, Low DA, Sheng K, Yang Y, Hu P. Respiratory motion-resolved, self-gated 4D-MRI using Rotating Cartesian K-space (ROCK): Initial clinical experience on an MRI-guided radiotherapy system. Radiother Oncol 2018; 127(3):467-473.

Keall PJ, Mageras GS, Balter JM, Emery RS, Forster KM, Jiang SB, Kapatoes JM, Low DA, Murphy MJ, Murray BR, Ramsey CR, Van Herk MB, Vedam SS, Wong JW, Yorke E. The management of respiratory motion in radiation oncology report of AAPM Task Group 76. Med Phys 4 2006;33(10):3874-3900.

Kerkmeijer LGW, Maspero M, Meijer GJ, van der Voort van Zyp JRN, de Boer HCJ, van den Berg CAT. Magnetic Resonance Imaging only Workflow for Radiotherapy Simulation and Planning in Prostate Cancer. Clin Oncol (R Coll Radiol) 2018;30(11):692-701.

Lagendijk JJ, Raaymakers BW, Van den Berg CA, Moerland MA, Philippens ME, van Vulpen M. MR guidance in radiotherapy. Phys Med Biol 2014;59(21):R349-369.

Li R, Lewis JH, Jia X, Zhao T, Liu W, Wuenschel S, Lamb J, Yang D, Low DA, Jiang SB. On a PCA-based lung motion model. Phys Med Biol 162011;56(18):6009-6030.

Paganelli C, Lee D, Kipritidis J, Whelan B, Greer PB, Baroni G, Riboldi M, Keall P. Feasibility study on 3D image reconstruction from 2D orthogonal cine-MRI for MRI-guided radiotherapy. J Med Imaging Radiat Oncol 2018;62(3):389-400.

Pang J, Sharif B, Fan Z, Bi X, Arsanjani R, Berman DS, Li D. ECG and navigator-free four-dimensional whole-heart coronary MRA for simultaneous visualization of cardiac anatomy and function. Magn Reson Med 2014;72(5): 1208-1217.

Piccini D, Littmann A, Nielles-Vallespin S, Zenge MO. Respiratory self-navigation for whole-heart bright-blood coronary MRI: methods for robust isolation and automatic segmentation of the blood pool. Magn Reson Med 2012;68(2):571-579.

Piccini D, Littmann A, Nielles-Vallespin S, Zenge MO. Spiral phyllotaxis: the natural way to construct a 3D radial trajectory in MRI. Magnetic resonance in medicine 2011;66( 4): 1049-1056.

Preiswerk F, Toews M, Cheng CC, Chiou JG, Mei CS, Schaefer LF, Hoge WS, Schwartz BM, Panych LP, Madore B. Hybrid MRI-Ultrasound acquisitions, and scannerless real-time imaging. Magn Reson Med 2017;78(3):897-908.

(56) References Cited

OTHER PUBLICATIONS

Raaymakers BW, Jurgenliemk-Schulz IM, Bol GH, Glitzner M, Kotte A, van Asselen B, de Boer JCJ, Bluemink JJ, Hackett SL, Moerland MA, Woodings SJ, Wolthaus JWH, van Zijp HM, Philippens MEP, Tijssen R, Kok JGM, de Groot-van Breugel EN, Kiekebosch I, Meij ers L TC, N om den CN, Sikkes GG, Doornaert P AH, Eppinga WSC, Kasperts N, Kerkmeijer LGW, Tersteeg JHA, Brown KJ, Pais B, Woodhead P, Lagendijk JJW. First patients treated with a 1.5 T MRI-Linac: clinical proof of concept of a high?precision, hig.

Raaymakers BW, Lagendijk JJ, Overweg J, Kok JG, Raaijmakers AJ, KerkhofEM, van der Put RW, Meijsing I, Crijns SP, Benedosso F, van Vulpen M, de Graaff CH, Allen J, Brown KJ. Integrating a 1.5 T MRI scanner with a 6 MV accelerator: proof of concept. Phys Med Biol 2009;54(12):N229-237.

Stehning C, Bomert P, Nehrke K, Eggers H, Stuber M. Free-breathing whole-heart coronary MRA with 3D radial SSFP and self-navigated image reconstruction. Magn Reson Med 2005;54(2):476-480.

Stemkens B, Paulson ES, Tijssen RHN. Nuts and bolts of 4D-MRI for radiotherapy. Phys Med Biol 2018;63(21):21 TR0I.

Stemkens B, Tijssen RH, de Senneville BD, Lagendijk JJ, van den Berg CA Image-driven, model- based 3D abdominal motion estimation for MR-guided radiotherapy. Phys Med Biol 2016;61(14):5335-5355.

Tyagi N, Fontenla S, Zelefsky M, Chong-Ton M, Ostergren K, Shah N, Warner L, Kadbi M, Mechalakos J, Hunt M. Clinical workflow for MR-only simulation and planning in prostate. Radiat Oncol 2017; 12(1):119.

Walsh DO, Gmitro AF, Marcellin MW. Adaptive reconstruction of phased array MR imagery. Magnetic resonance in medicine 2000;43(5):682-690.

Winkelmann S, Schaeffter T, Koehler T, Eggers H, Doessel O. An optimal radial profile order based on the Golden Ratio for time-resolved Mri. IEEE Trans Med Imaging 2007;26(1):68-76.

Zhang Q, Pevsner A, Hertanto A, Hu YC, Rosenzweig KE, Ling CC, Mageras Gs. A patient-specific respiratory model of anatomical motion for radiation treatment planning. Med Phys 2007;34(12):4772-4781.

International Search Report & Written Opinion of the International Searching Authority issued in International Patent Application PCT/US2020/029724 dated Jul. 2, 2020.

* cited by examiner

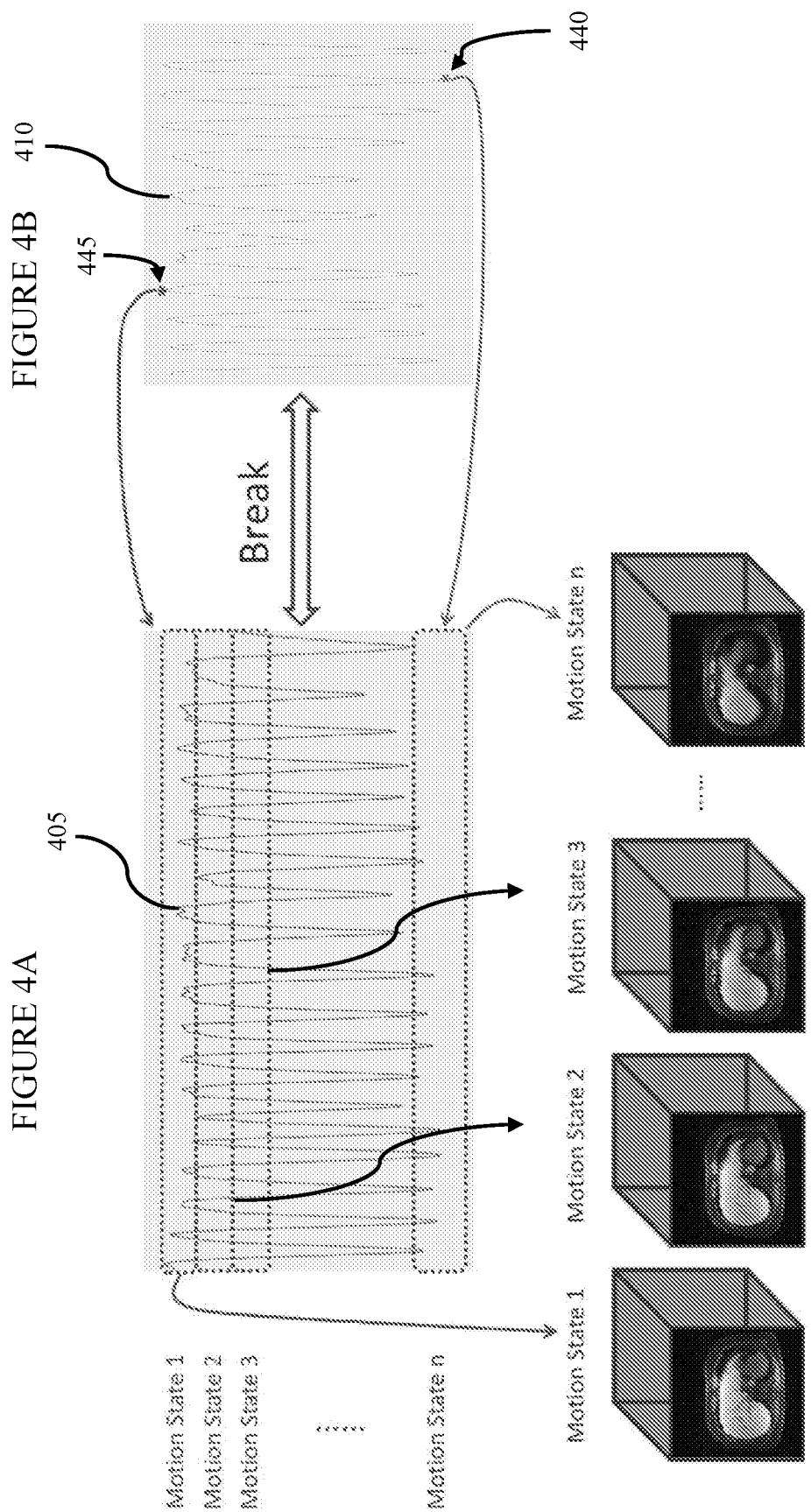

MAGNETIC RESONANCE SIGNATURE MATCHING (MRSIGMA) FOR REAL-TIME VOLUMETRIC MOTION TRACKING AND ADAPTIVE RADIOTHERAPY

CROSS-REFERENCE TO RELATED APPLICATIONS

This application is a National Stage Entry of PCT Application No. PCT/US2020/029724, filed Apr. 24, 2020, which further claims the benefit of and priority to U.S. Provisional Patent Application No. 62/838,922, filed Apr. 25, 2019, the entire contents of which are incorporated herein by reference in their entireties.

TECHNICAL FIELD

The present application presents a four-dimensional (4D) magnetic resonance imaging (MRI) approach with high spatial and temporal resolution that allows for real-time volumetric motion tracking in MRI-guided adaptive radiation therapy using a magnetic resonance linear accelerator (MR-Linac), and more specifically to a 4D MRI approach with very low latency (e.g., less than 0.2 seconds) to track organ motion in real-time, where latency is defined as the time period between the event and the generation of the image, which is given by the sum of acquisition time and reconstruction time.

BACKGROUND

Accurate and precise treatment delivery is required in radiotherapy to maximize irradiation in the tumor and to minimize toxicity in healthy tissue surrounding the tumor (i.e., reduce collateral damage). This can lead to dose escalation in the tumor and potentially to reduction in the number of treatment fractions. Moving organs pose a significant challenge for image-guided adaptive radiotherapy, and as a result, approaches that enable reliable tumor motion tracking and compensation have gained significant attention recently. Among different imaging modalities, MRI is particularly attractive due to its superior soft tissue contrast and the absence of ionizing radiation, and new MR-Linac systems that combine an MRI scanner and a linear accelerator are now available for MRI-based adaptive radiotherapy. The complexity of tumor motion requires three-dimensional (3D) motion tracking, as it was acknowledged by the American Association of Physicists in Medicine (AAPM) Task Group 76, and this represents one of the major challenges for MR-Linac given the relatively slow imaging speed of MRI.

SUMMARY

Example embodiments of the disclosure relate to high-resolution real-time 4D MRI-based motion-tracking systems and processes that address the unmet need of volumetric motion tracking with very low latency. In various implementations, the MRI-based motion-tracking approach may include two steps: (1) offline learning of 3D motion states and motion signatures, and (2) online matching of high temporal resolution signature-only data acquired in real time with one of the pre-learned motion signatures and/or motion states. Offline learning is capable of generating a database of motion states and corresponding signatures by reconstructing one 3D image for each motion state from data acquired continuously over multiple motion cycles (e.g., any number of motion cycles deemed to sufficiently account for variations in motion, such as at least two motion cycles, 5 motion cycles, 10 motion cycles, 25 motion cycles, 50 motion cycles, etc.), and generating a unique motion signature representing each motion state. This may be performed because, for example, major physiological motion, such as respiratory motion, occurs (pseudo-)periodically. The number of motion states can be determined according to the total acquisition time and can be adapted for different applications. In various implementations, the motion signature can be extracted directly from the imaging data or can be acquired explicitly as additional navigators. Acquisition of each signature can be very fast (e.g., about 100 to 200 milliseconds (ms)).

In various embodiments, online matching may be performed during the treatment period in the context of radiation therapy, in which case online matching may involve acquiring signature data only to generate online signatures without the need to reconstruct an image. This helps ensure that data acquisition can be fast enough for tracking organ motion in real time. The 3D motion state whose (offline) signature best matches (e.g., is most or otherwise sufficiently correlated with, or otherwise closest to) the newly-acquired (online) signature data may then be selected from the pre-learned database as the output image for this time point. The output image may then be used to make any adjustments that may be warranted by movements (even if only slight movements) of the target (e.g., the one or more tumors) resulting from movements by the subject (e.g., as a result of breathing or heartbeats). Potential embodiments of the disclosure are thus capable of shifting the acquisition and computational burden to an offline learning step, leaving simpler and rapid operations (e.g., acquisition of online signature data only and simpler signature matching that is relatively less computationally intensive) for the online matching step with dramatically reduced imaging latency. Example applications include real-time tumor motion tracking for adaptive radiotherapy using an MR-Linac system, and real-time organ motion tracking for characterization of organ function based on motion.

Various embodiments involve utilization of golden-angle k-space sampling, which can be implemented, for example, on a Cartesian or a non-Cartesian k-space grid, for certain practical implementations of the disclosure. Golden-angle sampling allows for a continuous data acquisition and offers a high level of incoherence along time, which facilitates arbitrary sorting of acquired data and combination with sparse reconstruction (compressed sensing). This helps enable the acquisition of 3D motion states with high spatial resolution within feasible scan times. Moreover, in various implementations, motion signatures can be extracted directly from golden-angle acquisitions, or navigator data can be easily inserted explicitly to serve as motion signatures.

In various potential versions, implementing the MSIGMA approach may involve using a stack-of-stars golden-angle radial sampling scheme (see FIGS. 3A-3C). The stack-of-stars trajectory is a hybrid sampling scheme, in which in-plane $k_x$-$k_y$ encoding may be implemented using radial lines separated by 111.250 (golden-angle) and the slice encoding ($k_z$) may be implemented using a Cartesian grid. Since each radial line passes through the center of k-space, a navigator along the z dimension can be obtained directly from the raw data by applying an inverse Fourier transform along the $k_z$ line formed by the central $k_y$-$k_x$ positions. The vertical dashed lines in FIG. 3A show the $k_z$ line for each time point in $k_z$-t space and FIG. 3B shows the navigators in z-t plane, depicting navigator and/or signature data generated from the central points in the radial k-space line corresponding to each $k_z$ point, and FIG. 3C shows examples of respiratory signals detected during the offline learning step (left) and the online matching step (right), respectively.

In one aspect, various embodiments of the disclosure relate to a method for tracking 3D organ motion with very high spatial and temporal resolution. The method may be a magnetic resonance imaging (MRI)-based method. The method may be implemented by a computing device having an offline module and an online module. The offline module may be configured to learn motion signatures (e.g., based on imaging data acquired over multiple motion cycles). The online module may be configured to use a motion signature learned via the offline module. The method may comprise offline learning of pairs of motion states and motion signatures. The method may comprise online matching of high temporal resolution signature data with high spatial resolution 3D motion states.

In various embodiments, the method may comprise administering a radiotherapy to a subject. Offline learning may be performed before commencement of the radiotherapy. Online matching may be performed during the radiotherapy.

In various embodiments, offline learning may comprise reconstructing one 3D image for each motion state from data acquired continuously over multiple motion cycles and a unique motion signature representing each motion state.

In various embodiments, offline learning may comprise using a golden-angle stack-of-stars k-space sampling scheme. In-plane k-space dimensions $k_x$ and ky may be sampled using a radial trajectory. Through-plane k-space dimension kz may be sampled using a Cartesian trajectory.

In various embodiments, motion signatures may be directly extracted from the acquired data for each motion state using all of a central k-space to form projections along time across the organ of interest. At the central k-space, a difference between $k_x$ and ky may be zero.

In various embodiments, a 3D golden-angle radial sampling trajectory with kooshball geometry may be used during offline learning.

In various embodiments, offline learning may comprise explicitly inserting at least one of a 1D navigator, a 2D navigator, and/or a low-resolution 3D navigator as motion signature.

In various embodiments, offline learning may comprise using a 3D golden-angle Cartesian trajectory. Two-dimensional phase-encoding in the ky-kz plane may be segmented into different interleaves. Each interleave may rotated by the golden angle.

In various embodiments, 3D motion states may be reconstructed with high spatial resolution using a compressed sensing reconstruction. A sparsity constraint may be enforced to exploit correlations along a motion dimension.

In various embodiments, the method may comprise building a database of the pairs of motion states and motion signatures learned offline.

In various embodiments, online matching may comprise performing signature-only acquisitions. Online matching may comprise selecting a motion state with a signature correlated with (e.g., most highly correlated with or otherwise sufficiently correlated with) acquired data corresponding to real-time 3D motion tracking.

In various embodiments, online matching may be performed while applying radiotherapy to a subject.

In another aspect, various embodiments of the disclosure relate to a computer-implemented method of performing adaptive radiotherapy. The method may comprise detecting a motion state of a subject with very low latency, such as latency that is no greater than 0.2 seconds. The motion state may be detected using an imaging system. The imaging system may be used by or via a computing device capable of controlling imaging by the imaging system. The method may comprise identifying a predetermined motion signature with which the detected motion state is (e.g., most highly or sufficiently) correlated. The identifying may be performed by or via the computing device, such as by or via an online module of the computing system. The method may comprise adapting the radiotherapy based on the identified motion signature. The radiotherapy may be adapted so as to avoid, minimize, or otherwise reduce toxicity to healthy tissue. The radiotherapy may be adapted by or via the computing device.

In various embodiments, radiotherapy adapting may involve alignment and realignment, as needed, of the target (e.g., tumor) with a radiation beam. For example, adapting of radiotherapy may comprise aiming and re-aiming of a radiation beam, adjusting a shape of a radiation beam, adjusting an intensity of a radiation beam, repositioning of the subject (e.g., by moving a platform), and/or stopping and restarting delivery (i.e., adjusting timing) of a radiation beam (e.g., pausing radiation delivery when the target is expected to be out of the path of the radiation beam being delivered).

In various embodiments, the method may comprise tracking motion through one or more motion cycles of the subject during the radiotherapy. The motion may be tracked by or via the computing device. The method may comprise delivering radiotherapy during the one or more motion cycles. The radiotherapy may be adaptively delivered based on the correlation of detected motion states with motion signatures.

In various embodiments, radiotherapy may be adapted by adjusting a position of a radiation beam, a shape of a radiation beam, a timing of a radiation beam, an intensity of the radiation beam, and/or a position of the subject.

In various embodiments, the imaging system may include a magnetic resonance imaging (MRI) scanner.

In various embodiments, the radiotherapy may be performed using at least a linear accelerator.

In various embodiments, the predetermined motion signature may be learned through offline learning of pairs of motion states and motion signatures. The predetermined motion signature may be learned by or via an offline module of the computing device.

In various embodiments, identifying the predetermined motion signature may be part of online matching of high temporal resolution signature data with high spatial resolution 3D motion states. The online matching may be performed by or via an online module of the computing device.

In another aspect, various embodiments of the disclosure relate to a system for performing adaptive radiotherapy. The system may comprise an imaging system. The imaging system may be configured to detect a motion state of a subject. The system may comprise a therapeutic system. The therapeutic system may be configured to apply radiation to the subject. The system may comprise a computing device. The computing device may be configured to control the imaging system and/or the therapeutic system to perform radiotherapy on the subject. The computing device may have one or more processors and a memory storing instructions that, when executed by the one or more processors, cause the one or more processors to perform specific functions. The one or more processors may be configured to control the imaging system to detect a motion state of the subject. The one or more processors may be configured to identify a predetermined motion signature with which the detected motion state is correlated (e.g., most highly correlated). The one or more processors may be configured to control the therapeutic system to adapt the radiotherapy based on the motion signature.

In various embodiments, the motion signature may be predetermined by or via an offline module of the computing device.

In various embodiments, correlating the predetermined motion signature with the detected motion state may be performed by or via an online module.

In various embodiments, the imaging system may include a magnetic resonance imaging (MRI) scanner.

In various embodiments, the radiotherapy may be performed using at least a linear accelerator.

In another aspect, various embodiments relate to a computer-implemented magnetic resonance imaging (MRI) method for tracking 3D organ motion using high spatial resolution 3D motion states and high temporal resolution motion signature data. The method may comprise performing offline learning, which may comprise generating pairs of 3D motion states and offline motion signatures based on MRI images acquired during one or more motion cycles. The method may comprise generating an online motion signature, which may be generated without image reconstruction. The method may comprise performing online signature matching, which may comprise comparing the online motion signature with offline motion signatures to identify a corresponding 3D motion state. The motion state may be identified so as to account for motion during radiotherapy by adapting delivery of radiation according to target position and/or target shape (which may change as a result of, e.g., movements of the subject), and thereby improve treatment accuracy to reduce toxicity to healthy tissue surrounding a target of the radiotherapy.

In another aspect, various embodiments also relate to a system for performing adaptive radiotherapy. The system may comprise an imaging system configured to detect a motion signature of a subject. The system may comprise a therapeutic system configured to apply radiation to the subject (e.g., one or more radiation beam emitters). The system may comprise a computing device configured to control the imaging system and the therapeutic system to perform radiotherapy on the subject. The computing device may have one or more processors and a memory storing instructions that, when executed by the one or more processors, cause the one or more processors to perform specific functions. The computing device may be configured to detect a motion signature of the subject. The motion signature may be detected using the imaging system (which may include an MRI scanner). The computing device may be configured to identify a predetermined motion signature with which the detected motion signature is most (or sufficiently) highly correlated (by, e.g., performing correlation analysis). The computing system may be configured to select a predetermined 3D motion state that corresponds to the identified predetermined motion signature. The computing device may be configured to adapt the radiotherapy based on the selected 3D motion state. The radiotherapy may be adapted via the therapeutic system (or control thereof). The radiotherapy may be adapted as to account for motion of the subject during radiotherapy. The radiotherapy may be adapted to increase a proportion of radiation applied to a target (e.g., one or more tumors) relative to (healthy) tissue surrounding the target.

In various embodiments, the system may comprise a movable platform that may be controllable via the computing device. The computing device may be configured to adapt the radiotherapy in part by, for example, moving the platform (e.g., to make small adjustments). The platform may be moved, for example, so as to maintain the target in a path of one or more radiation beams.

In another aspect, various embodiments relate to a computer-implemented method of performing adaptive radiotherapy. The method may comprise detecting a motion signature of a subject. The motion signature may be detected with latency less than 0.2 seconds. The motion signature may be detected by a computing device using an imaging system. The method may comprise identifying a predetermined motion signature with which the detected motion signature is most highly correlated. The predetermined motion signature may be identified by the computing device using the imaging system to detect the motion signature. The method may comprise selecting the predetermined 3D motion state that corresponds to the identified predetermined motion signature. The method may comprise adapting the radiotherapy based on the selected 3D motion state. The radiotherapy may be adapted to a new target location and/or target shape so as to increase treatment accuracy and thereby reduce toxicity to healthy tissue. The radiotherapy may be adapted by the computing device.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

FIG. 4A depicts offline learning and FIG. 4B depicts online matching steps, separated by a break interval, according to potential embodiments. An example of the break interval can be the transition from beam-off to beam-on for an MR-Linac system. During offline learning, the motion database may be generated where each entry is given by the pair of motion signature (line 405) and motion state (3D image). During online matching, online signature data (line 410) are matched to the corresponding offline signature (405 line). Here, each offline motion signature, represented by dashed rectangular box, is defined as a window or range.

Figure 5A:
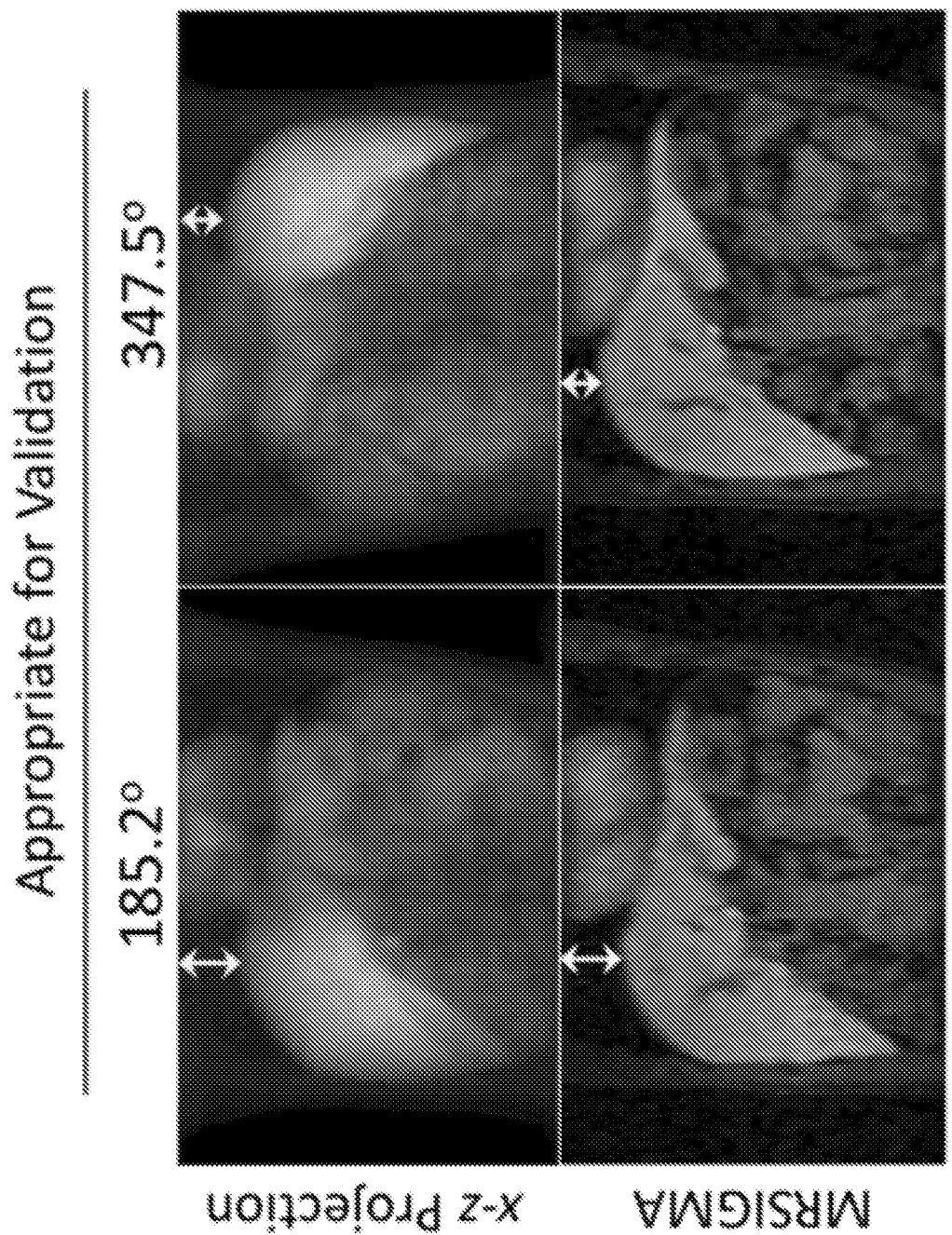
Figure 5B:
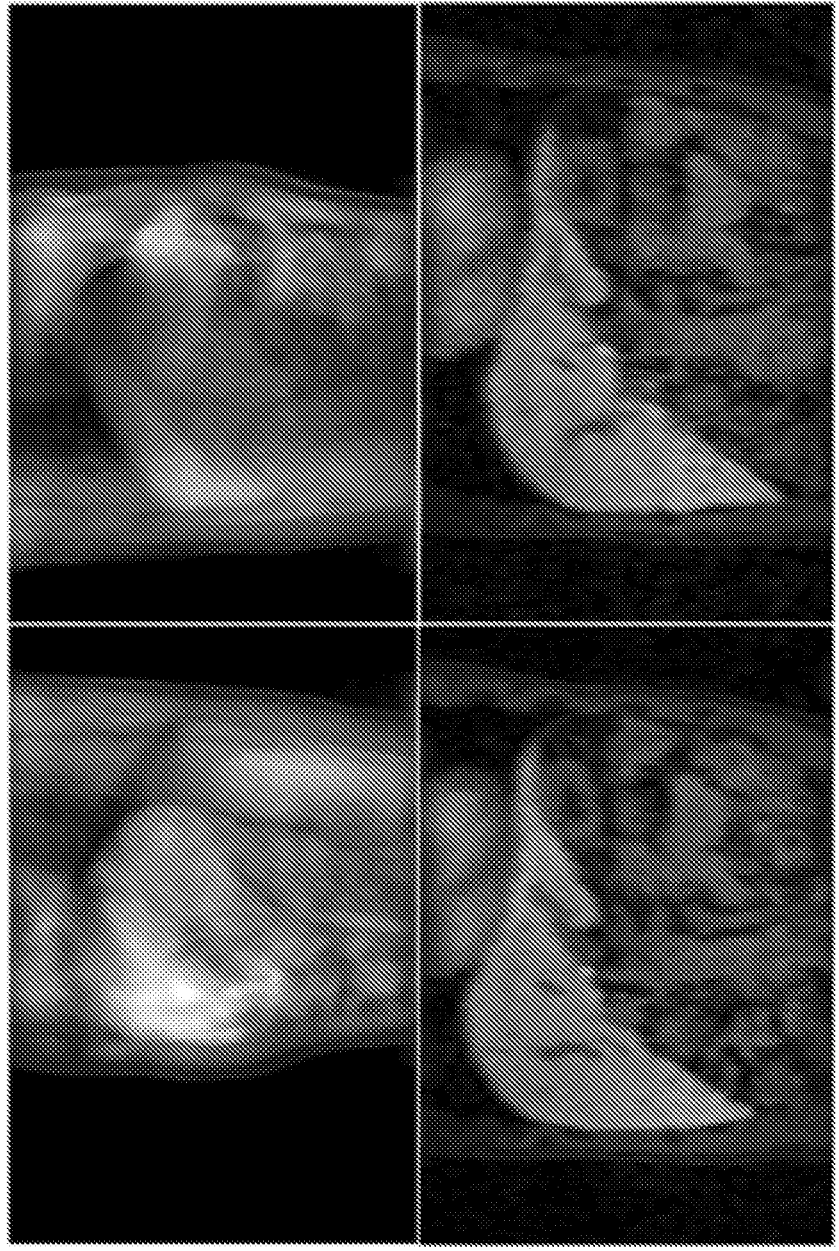

FIGS. 5A and 5B provide a comparison of x-z 2D projections with corresponding 3D images obtained with example motion tracking systems at different acquisition angles, according to potential embodiments. The distance of the liver dome with respect to the top edge of the FOV (vertical two-way arrows) was measured for both online-generated 3D images and real-time 2D projections to validate the accuracy of embodiments of the motion tracking system. These images also indicate that the liver dome can be seen in certain angles (FIG. 5A) and cannot be visualized clearly in some angles (FIG. 5B), and thus, the distance was only measured in the acquisitions angle from which the liver dome can be visualized in this implementation.

Figure 6:
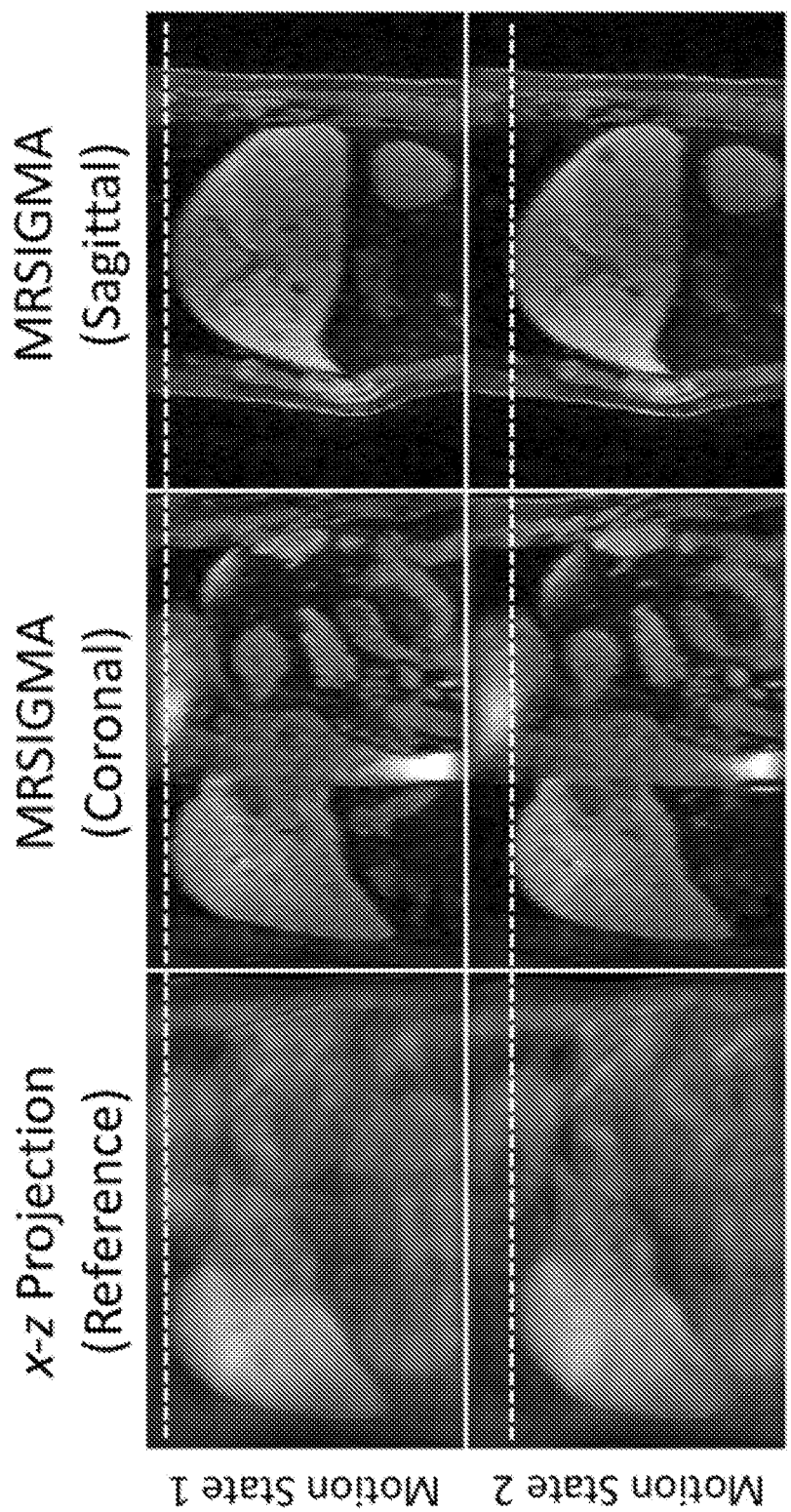

FIG. 6 provides a comparison of x-z 2D projections with corresponding 3D images obtained with a motion tracking system at different motion states in a first patient, according to potential embodiments. The x-z 2D projections, which serve as the online motion signature data, are treated as reference to validate the motion pattern in embodiments of the disclosed motion tracking approach. This example shows that the motion tracking system is able to generate high-resolution 3D images in real time, with its motion pattern well-correlated with the reference 2D projection (horizontal dashed lines).

Figure 7:
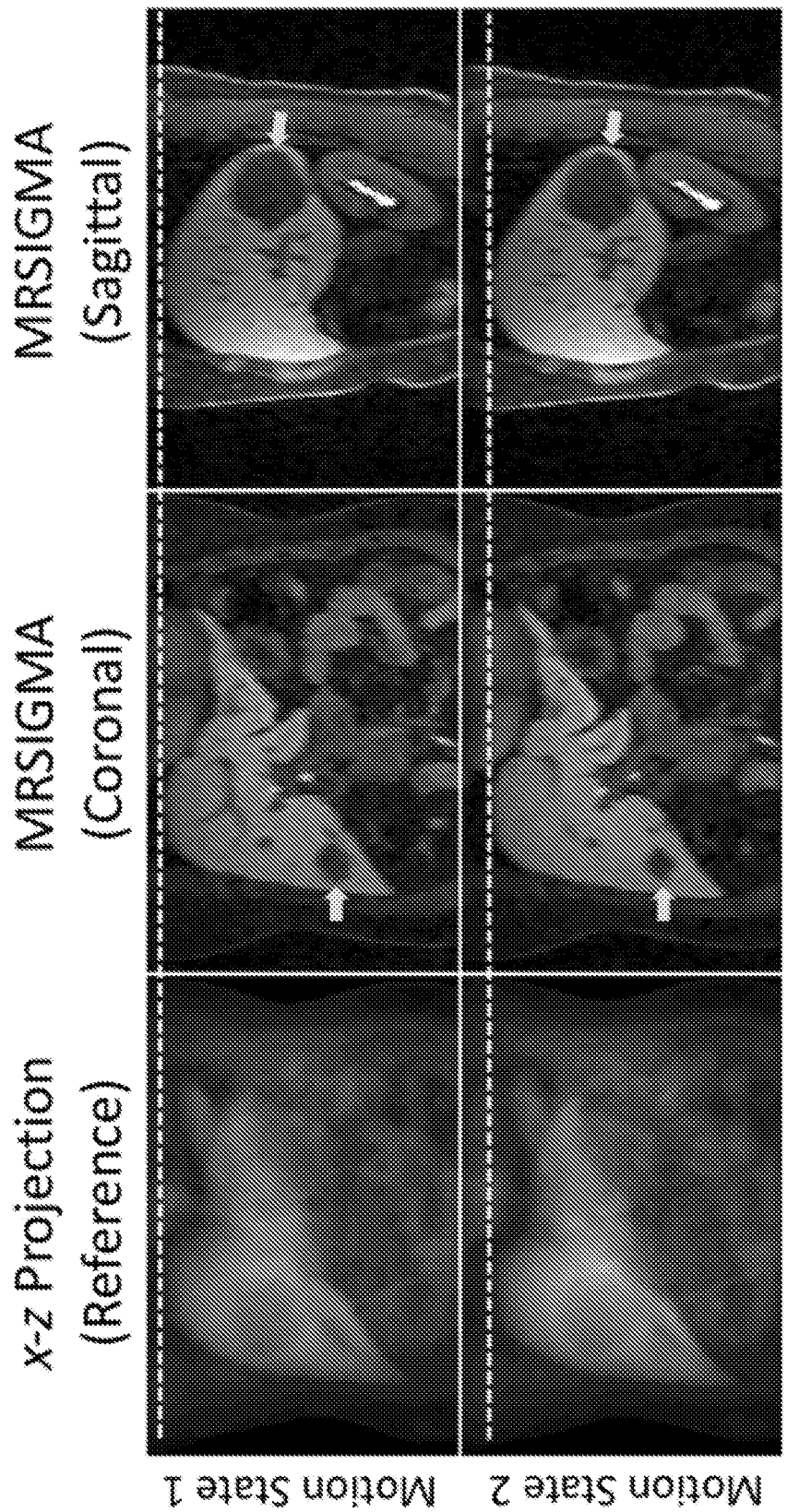

FIG. 7 provides a comparison of x-z 2D projections with corresponding 3D images obtained with a motion tracking system at different motion states in a second patient, according to potential embodiments. As in FIG. 6, the motion tracking system may generate high-resolution 3D images with a motion pattern well-correlated with the reference 2D projection (horizontal dashed lines). The arrows indicate suspicious lesions that can be well visualized in both coronal and sagittal planes.

Figure 8:
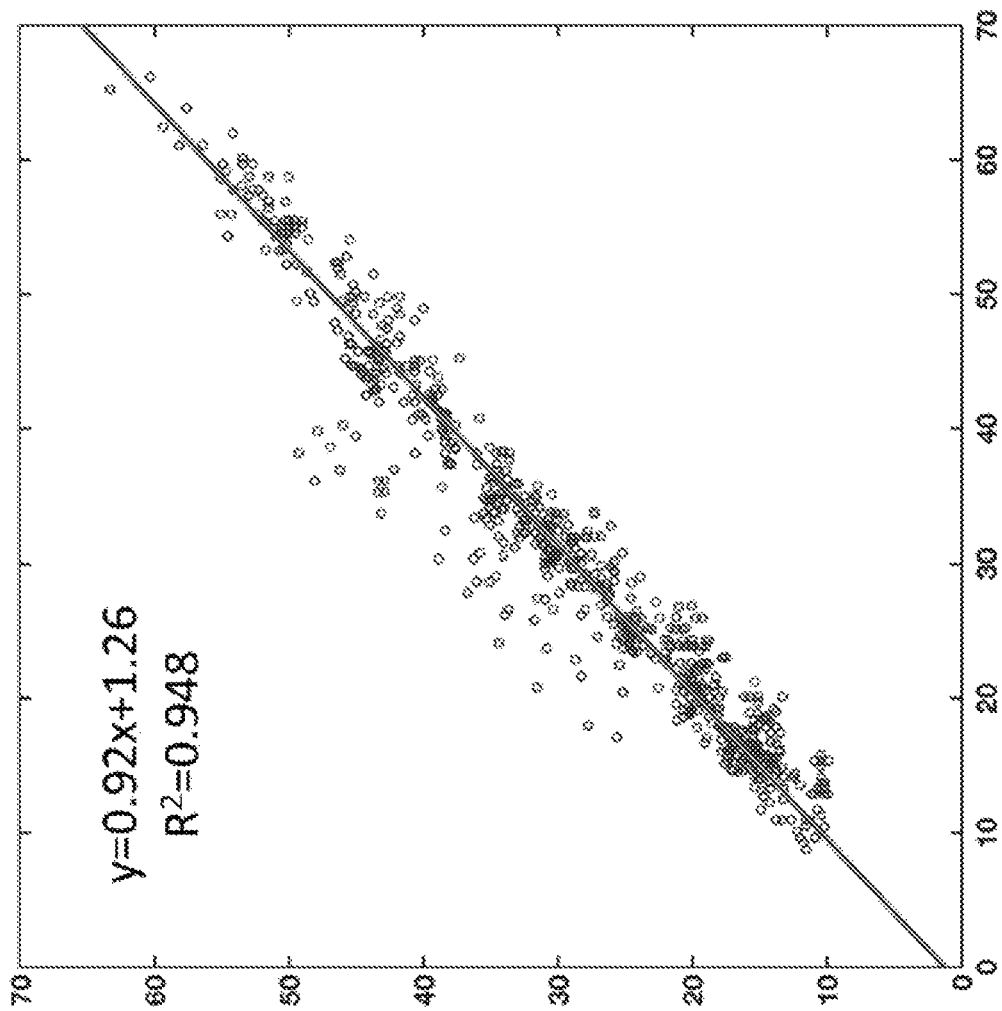

FIG. 8 provides a linear correlation plot to assess the correlation of motion displacement measured from online-generated 3D images and x-z 2D projection profiles acquired in real time, according to potential embodiments. The slope of the plot is 0.92 and the intercept was 1.26 millimeters, with an R-square of 0.948. These results indicate excellent correlation of the motion displacement measured using these two types of images.

Figure 9:
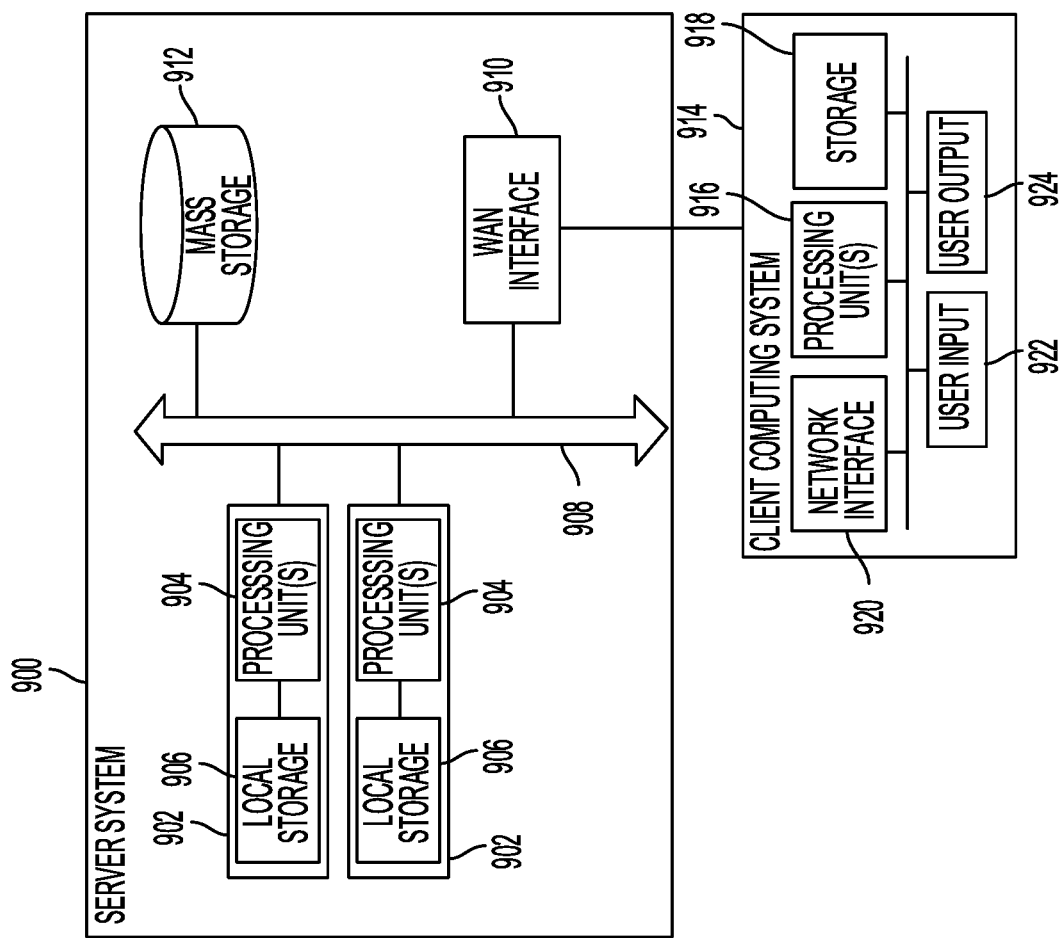

FIG. 9 shows a simplified block diagram of a representative server system and client computer system usable to implement certain embodiments of the present disclosure.

Figure 10:
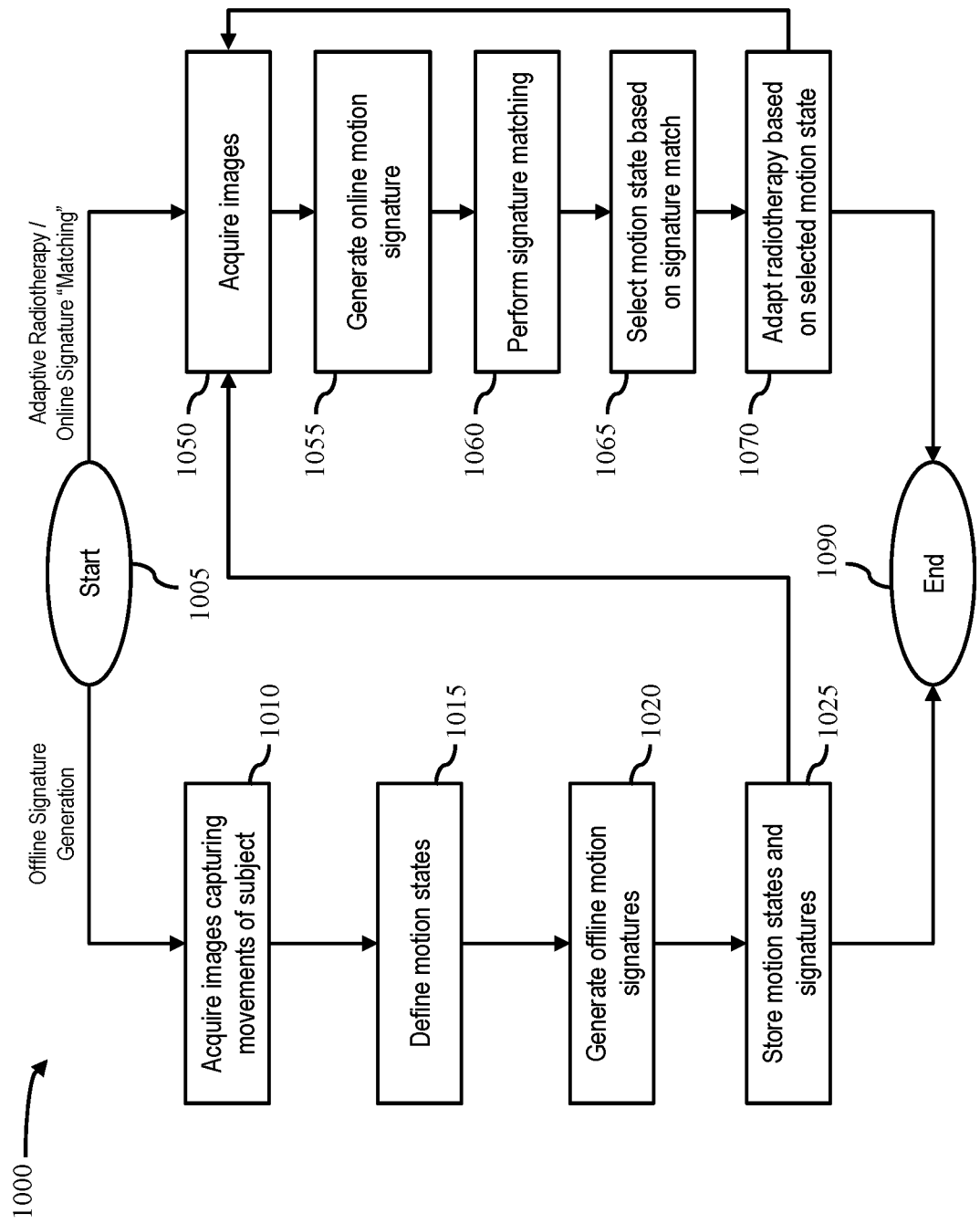

FIG. 10 illustrates example processes for offline signature generation and online correlation of motion signatures during adaptive radiotherapy, according to various potential embodiments.

The foregoing and other features of the present disclosure will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, may be arranged, substituted, combined, and designed in a wide variety of different configurations, all of which are explicitly contemplated and make part of this disclosure.

Current MRI technology is not able to deliver acquisition and reconstruction of 3D data with sufficient spatial resolution in "real-time" for tumor motion tracking. Even with the latest advances in rapid imaging, such as compressed sensing and non-Cartesian sampling, real-time MRI is still limited to 2D acquisitions, which often suffers from through-plane motion misregistration and suboptimal interpretation of motion. Thus, an approach allowing high resolution 3D motion tracking in "real-time" is highly-desirable.

To track volumetric tumor motion in real-time for potential applications of MRI-guided adaptive radiation therapy in moving organs, studies have proposed to perform fast 2D cine imaging in three orthogonal directions simultaneously, from which a pseudo-3D images can be estimated for deriving volumetric tumor motion information. Another approach involves aiming to calculate a patient-specific motion model that can link a 4D time-resolved data acquisition over multiple motion cycles with real-time 2D cine imaging to generate pseudo-3D images. However, these methods suffer from uncertainties in the motion model and interpolation artifacts, and any error during the conversion step may be propagated through the entire treatment workflow. Additionally, the conversion of 2D images to pseudo-3D images often involves a computationally expensive calculation step, leading to high latency without immediate feedback, thus restricting real-time adaptive treatment delivery. Although different accelerated 4D MRI approaches have also been proposed for MRI-guided radiation therapy, these approaches still require relatively long acquisition times and/or complicated image reconstruction, limiting their real-time capability and thus ultimate application in a clinical setting.

Figure 1:
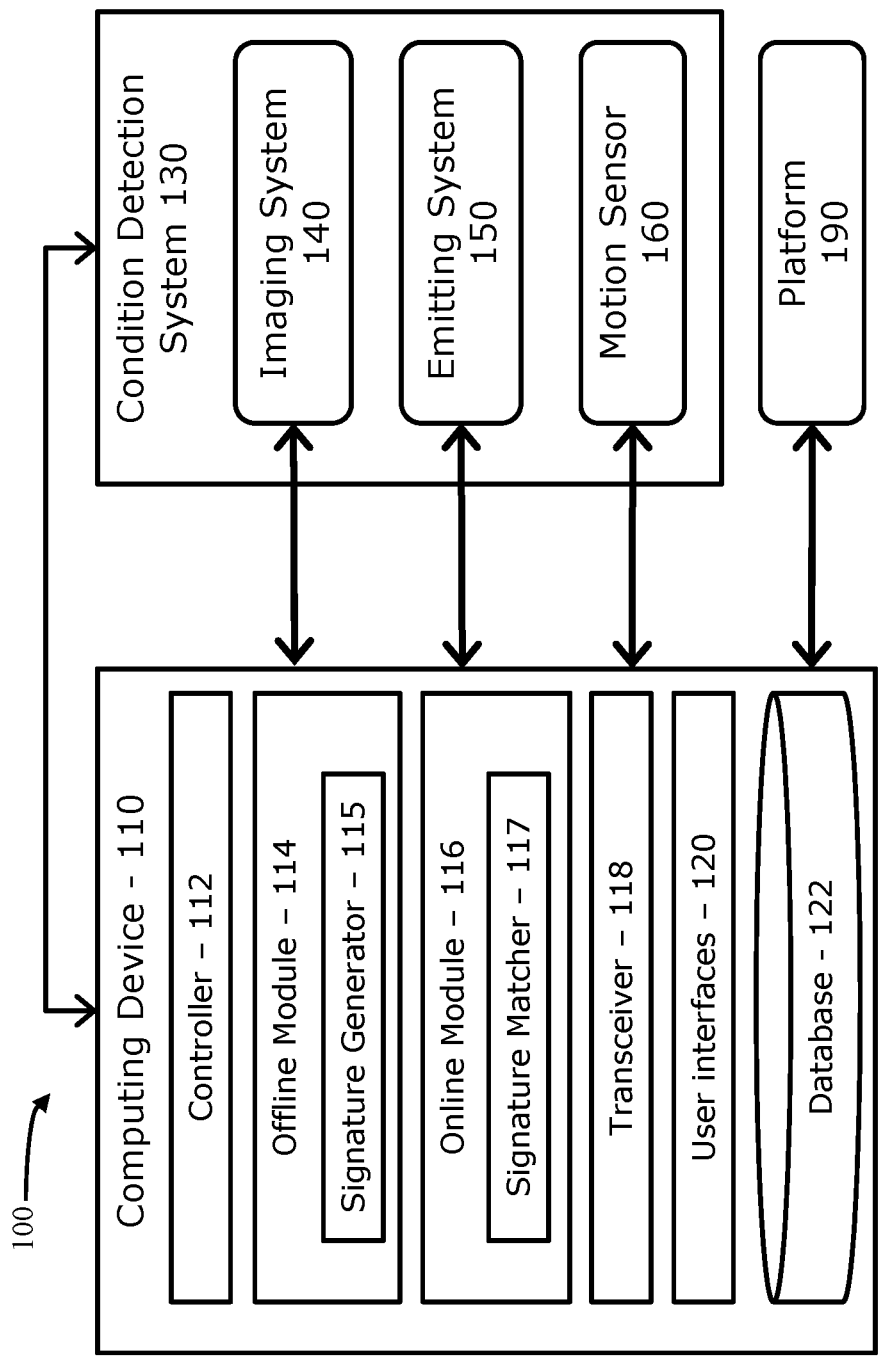
FIG. 1 depicts an example system for implementing disclosed motion tracking approach, according to potential embodiments.

Referring to FIG. 1, in various embodiments, a system 100 may include a computing device 110 (or multiple computing devices, co-located or remote to each other), an imaging system 140 (which may include, e.g., an MRI scanner or other imaging devices and sensors), an emitting system 150 (which may include, e.g., a linear accelerator and/or one or more other treatment devices), and and/or a motion sensor 160. In various implementations, the imaging system 140, the emitting system 150, and/or the motion sensor 160 may be integrated into one condition detection system 130 (such as an MR-Linac). In certain implementations, computing device 110 (or components thereof) may be integrated with one or more of the condition detection system 130, imaging system 140, emitting system 150, and/or motion sensor 160. The condition detection system 130, imaging system 140, emitting system 150, and/or motion sensor 160 may be directed to a platform 190 on which a patient or other subject can be situated (so as to image the subject, apply a treatment or therapy to the subject, and/or detect motion by the subject). In various embodiments, the platform 190 may be movable (e.g., using any combination of motors, magnets, etc.) to allow for positioning and repositioning of subjects (such as micro-adjustments due to subject motion).

The computing device 110 (or multiple computing devices) may be used to control and/or receive signals acquired via imaging system 140, emitting system 150, and/or motion sensor 160 directly. In certain implementations, computing system 110 may be used to control and/or receive signals acquired via condition detection system 130. The computing device 110 may include one or more processors and one or more volatile and non-volatile memories for storing computing code and data that are captured, acquired, recorded, and/or generated. The computing device 110 may include a controller 112 that is configured to exchange control signals with condition detection system 130, imaging system 140, emitting system 150, motion sensor 160, and/or platform 190, allowing the computing device 110 to be used to control the capture of images and/or signals via the sensors thereof, and position or reposition the subject. The computing device 110 may also include an offline module 114 (used interchangeably with offline learning module), which includes a signature generator 115, configured to perform the computations and analyses discussed herein with respect to offline learning (e.g., learning that occurs apart from a treatment), and an online module 116, which includes a signature matcher 117, configured to perform the computations and analyses discussed herein with respect to online matching (e.g., real-time motion detection during a treatment).

It is noted that "matching" or identifying a "match" does not require equivalency (i.e., does not require exact matches) but rather determining which two are sufficiently "close" (e.g., sufficiently highly correlated) when not identical. "Matching" or otherwise sufficient "closeness" may be determined, for example, through correlation analysis, such as linear correlation between the input and target signals, or clustering analysis, where one property of the input signal (e.g., amplitude) is within the limits defined for each cluster of the target signal.

A transceiver 118 allows the computing device 110 to exchange readings, control commands, and/or other data with condition detection system 130, imaging system 140, therapeutic system 150, motion sensor 160, and/or platform 190 wirelessly or via wires. One or more user interfaces 120 allow the computing system to receive user inputs (e.g., via a keyboard, touchscreen, microphone, camera, etc.) and provide outputs (e.g., via a display screen, audio speakers, etc.). The computing device 110 may additionally include one or more databases 122 for storing, for example, signals acquired via one or more sensors, signatures, etc. In some implementations, database 122 (or portions thereof) may alternatively or additionally be part of another computing device that is co-located or remote and in communication with computing device 110, condition detection system 130, imaging system 140, therapeutic system 150, motion sensor 160, and/or platform 190.

Figure 2A:
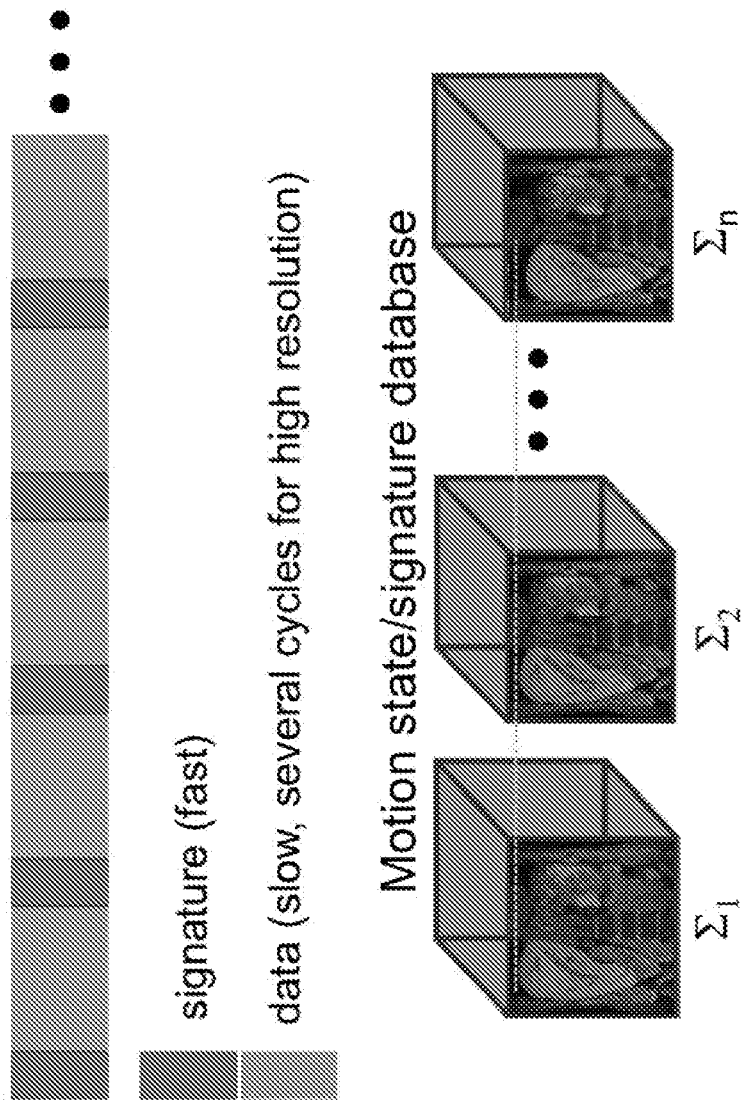
FIGS. 2A and 2B provide a graphical overview of motion tracking according to potential embodiments, with FIG. 2A depicting offline learning that acquires signature and 3D imaging data over multiple respiratory cycles to create a database of high-resolution motion states, and FIG. 2B depicting online matching that acquires only signature data at high temporal resolution. From the database with motion states and motion signatures, the 3D motion state whose signature best matches the newly-acquired signature data is selected. Real-time 3D motion tracking may be accomplished by performing all the time-consuming acquisition and reconstruction tasks during offline learning and leaving just signature data acquisition and signature matching for online matching to minimize latency.
Figure 2B:

Various embodiments of the disclosure relate to systems and methods for motion tracking, which may involve (1) offline learning of 3D motion states and motion signatures, and (2) online matching of signature-only data acquired in real-time (i.e., with an acquisition latency less than 0.2 seconds) with one of the pre-learned or pre-computed motion signatures or motion states. In FIGS. 2A and 2B, this is illustrated for tracking 3D respiratory motion. Offline learning (via, e.g., offline module 114) can involve acquiring signature and 3D imaging data over multiple respiratory cycles to create database 122 of high resolution motion states. Online matching (via, e.g., online module 116) can involve acquiring signature-only data at high temporal resolution. From the motion state and signature database 122, the 3D motion state whose signature best matches the newly-acquired signature data may be selected (e.g., via online module 116). In various embodiments, real-time 3D motion tracking may be accomplished by having offline module 114 perform all (or at least some) of the time-consuming acquisition and reconstruction work in an offline learning phase, while leaving just online signature acquisition and correlation analysis for the online module 116 in an online matching step, thereby minimizing or otherwise significantly reducing latency.

In various embodiments of the disclosure, the offline module 114 may perform an offline learning step that generates a database 122 of motion states with corresponding (offline) signature entries by acquiring and reconstructing a 4D motion-resolved image-set over multiple motion cycles and a unique motion signature to represent each motion state.

The online module 116 may perform an online matching step that involves acquiring signature data only (fast)—i.e., without image reconstruction—and selecting one of the pre-learned 3D motion state whose (offline) signature best matches the newly-acquired (online) signature data. System 100 may use one or more techniques to acquire datasets. In some implementations, system 100 may acquire 3D datasets (e.g., for an organ such as the liver) using a stack-of-stars golden-angle sequence. The accuracy of motion tracking may be validated against x-z 2D projections acquired in real time. The system 100 is configured for low latency (i.e., the sum of acquisition time and reconstruction time) to enable real-time or near real-time volumetric motion tracking. Total latency for the online matching may be, for example, about 330 ms or less, including time for acquisition of online motion signature (e.g., about 178 ms or less) and time for matching (e.g., about 150 ms or less). In example embodiments, the described motion tracking approach implemented by system 100 shifts the acquisition and reconstruction burden to an offline learning process and performs volumetric motion tracking with very low latency in an online matching process. In various implementations, system 100 may be targeted to MRI-guided adaptive radiation therapy in moving organs.

In various embodiments, the offline module 114 generates (for storage in database 122) motion states and corresponding signatures by reconstructing one 3D image for each motion state from data acquired continuously over multiple motion cycles and a unique motion signature representing each motion state. This may be performed because major physiological motion, such as respiratory motion, occurs (pseudo-) periodically. The number of motion states can be determined by offline module 114 according to the total acquisition time and can be adapted for different applications. The offline module 114 can extract the motion signature directly from the imaging data or can acquire the motion signature explicitly as additional navigators. An important point for various implementations of system 100 is that the acquisition of each signature is very fast (e.g., about 100 to 200 ms in various versions).

In various implementations, the online matching step, to be performed (via online module 116) during the treatment period in the context of radiation therapy, acquires signature data only. This helps ensure that data acquisition can be fast enough for tracking organ motion in real time. The 3D motion state whose signature best matches the newly-acquired signature data is then selected from the pre-learned database as the output image for this time point. Computing device 110 shifts the acquisition and computational burden to the offline learning step (performed via offline module 114), leaving simple and rapid operations (e.g., acquisition of signature data only and simple signature matching) for the online matching step (performed via online module 116) with dramatically reduced imaging latency.

Described is a combination of golden-angle radial k-space sampling (further described in Winkelmann et al. (2007), cited below) and XD-GRASP reconstruction (further described in Feng et al. (2016), cited below) for implementing the disclosed motion-tracking approach, in potential embodiments. Golden-angle radial sampling enables continuous data acquisitions and arbitrary sorting of acquired data into different motion states. The high level of incoherence along time provided by golden-angle radial sampling also facilitates the use of compressed sensing reconstruction approaches, which speed up the generation of the database of motion states. Moreover, radial sampling also allows self-navigation, from which a motion signal can be directly extracted from the acquired data as motion signatures, as further described below.

Figure 3A:
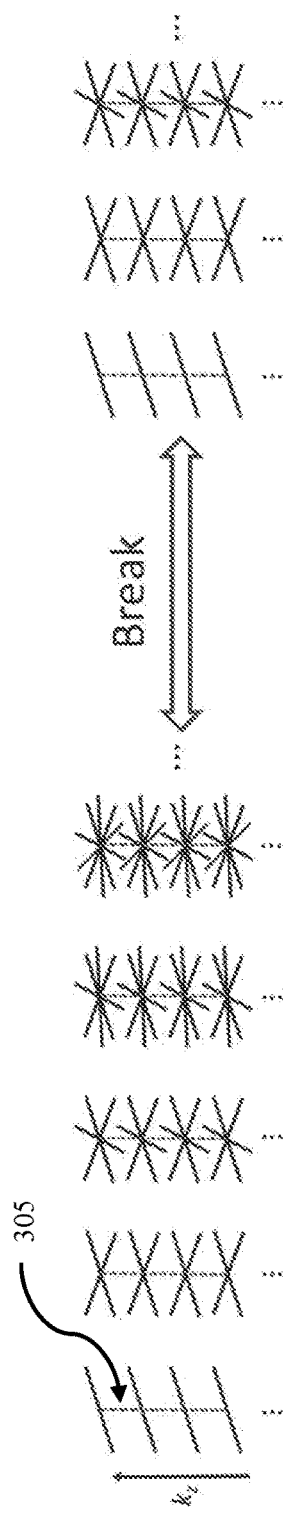
FIG. 3A depicts stack-of-stars golden-angle radial sampling for motion tracking.
Figure 3B:
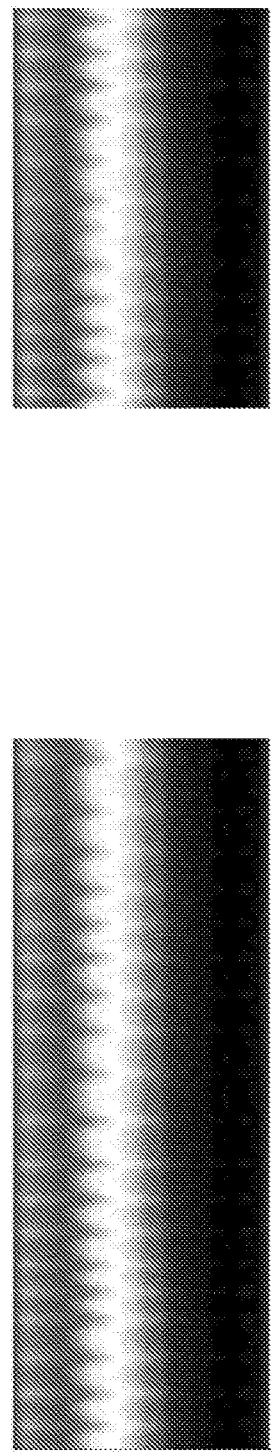
FIG. 3B depicts high temporal resolution signature data generated by taking a projection along the z-dimension for each angle, and FIG. 3C provides examples of respiratory signals produced during offline learning (curve on left side) and online matching (curve on right side), according to potential embodiments.
Figure 3C:
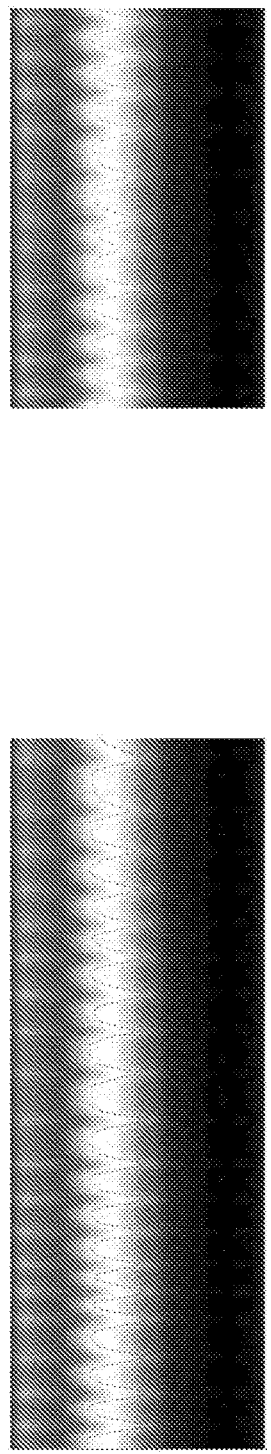

According to various potential embodiments, offline module 114 performs 3D radial acquisitions using a stack-of-stars golden-angle sampling trajectory (FIGS. 3A-3C), in which the in-plane $k_x$-$k_y$ encoding may be implemented using radial lines rotated by a golden angle (111.25°) and the slice encoding ($k_z$) may be implemented on a Cartesian grid. Since each radial line passes through the center of k-space, offline module 114 obtains a navigator along the z dimension directly from the acquired k-space data by applying an inverse fast Fourier transform (FFT) along each $k_z$ line formed by the central $k_x$-$k_y$ k-space points, in various embodiments. The vertical dashed lines (305) in FIG. 3A show the $k_z$ profiles for each time point in $k_z$-t space, and FIG. 3B shows corresponding navigators in the z-t plane. FIG. 3C shows examples of respiratory signals detected during the offline learning step and the online matching step, respectively. A more detailed description of an example motion detection algorithm can be found in Feng et al. (2018), cited below.

FIGS. 4A and 4B show k-space data sorting and XD-GRASP reconstruction for generation of offline motion states for signature database 122 and online signature matching by computing device 110. Specifically, based on a respiratory motion signal, computing device 110 first sorts 3D k-space data into a number of undersampled motion states. Computing device 110 then reconstructs the whole 4D k-space data, where the fourth dimension represents motion states, using a multicoil compressed sensing (sparse) algorithm or approach that exploits correlations along the motion dimension by minimizing differences between adjacent frames (i.e., minimizing total variation along motion states). In various implementations, the reconstruction algorithm applied by computing device 110 aims to solve the following optimization problem:

$$d = \arg_d \min \frac{1}{2} \|Ed - u\|_2^2 + \lambda \|Td\|_1 \qquad \text{Eq. 1}$$

Here, E is the acquisition or encoding operator (mapping from $k_x$-$k_y$-$k_z$-t-coil space to x-y-z-t space), d is the 4D image to be reconstructed (x-y-z-t), u is the acquired multicoil k-space data sorted into multiple motion states ($k_x$-$k_y$-$k_z$-t-coil space), λ is a regularization parameter controlling the balance between the data consistency (the left term) and the promotion of sparsity (the right term). T is the first-order finite differences operator applied along the motion state dimension (t represents the motion state dimension). As discussed above, in some embodiments, the online module 116 only acquires signature data for extracting motion signature, which can be acquired with high temporal resolution without an explicit reconstruction step. Once the online motion signature (curve 410 in FIG. 4B) is computed, online module 116 compares the motion signature to the offline motion signatures in the database 122 (e.g., using correlation analysis). Online module 116 selects a 3D motion state (with an offline signature presenting the best match with the online signature) as the output motion state at the current time point. The process of acquiring signature data (central $k_x$-$k_y$ point for each $k_z$), computing online signature (inverse Fourier transform and filtering) and simply online (correlation-based) signature matching minimizes the latency by reducing both data acquisition time and computation time.

In an in vivo test, 15 patient liver 3D datasets previously acquired using a prototype fat-saturated stack-of-stars golden-angle sequence on a 3.0T MRI scanner were retrospectively collected to test an implementation of the disclosed motion tracking approach. Relevant parameters of the datasets included: matrix size=256×256×44, FOV=320× 320×216 mm$^3$, voxel size=1.25×1.25×5 mm$^3$, TR/TE=3.40/ 1.68 ms, flip angle=100 and bandwidth=600 Hz/pixel. A total of 1000 spokes were acquired during free-breathing for each $k_z$ position with 80% partial Fourier applied along the $k_z$ dimension, resulting in a total scan time of 178 seconds. The stack-of-stars acquisition was performed in a way that all the partitions for a given rotation angle were acquired linearly before moving to the next acquisition angle. For each patient, the radial scan was added to the end of the clinical exam, approximately 20 minutes after the injection of the Gd-EOB-DTPA.

Offline learning was performed using spokes 6-905 (900 spokes) and online matching was performed using spokes 906-1000 (95 spokes). The first 5 spokes were discarded since they were acquired in the beginning and were not at a steady state. For offline learning, the respiratory motion signal was extracted from the centers of k-space, as described above. Based on the motion signal, all the 900 spokes were sorted into 10 motion states spanning from expiration to inspiration, followed by XD-GRASP reconstruction. The sorting process was performed in a way that each motion state had a same number of spokes (90 spokes). Reconstruction was implemented in MATLAB using a non-linear conjugate gradient algorithm to solve Equation 1 above and was performed in a workstation with OSX operation system, 8-core CPU and 64 GB memory. Coil sensitivity maps were estimated from a 3D image reconstructed by averaging all the acquired spokes using the adaptive combination method (see Walsh et al. (2000)).

Online matching (for 95 spokes) was performed to generate corresponding 95 3D images with a temporal resolution of 0.178 seconds per volume (178/1000 seconds). Online signature data for each spoke were given by the 2D x-z plane resulting from 2D FFT along $k_x$ and $k_z$, and signatures were extracted as corresponding respiratory motion signal, as performed in the offline learning step. The matching process is outlined in FIGS. 4A and 4B. Specifically, the offline motion signatures were chosen as different non-overlapping windows (dashed rectangular box, FIG. 4A) in the implementation representing different motion ranges. Given an online motion signature (e.g., star symbols 440, 445), a pre-learned motion state whose motion range covers the target signature was selected by checking which window a newly-acquired motion signature belongs to. The 3D motion image or motion state corresponding to this window is then selected as the output motion state for the current time point. If an online motion signature falls outside all the respiratory windows, (e.g., in case of deeper breathing), the matching of this signature is skipped and the process moves to the next time point. However, this is not expected to occur often since a sufficient amount of data can be acquired during offline learning to cover most respiratory positions.

Embodiments of the disclosure were evaluated using a strategy that correlated the organ motion displacement in the online-generated 3D images with the motion displacement in corresponding x-z 2D real-time projections, which were obtained by applying a 2D inverse FFT on the online signature data (2D planes in $k_x$-$k_z$ dimension for the last 95 spokes). Since these online signature data were acquired in real time, they can be treated as a reference of motion displacement here. The analysis was performed in MATLAB. Specifically, both the online-generated 3D images and real-time 2D projections were first interpolated (zero-filling in k-space) along the slice dimension to obtain a voxel size matching the in-plane resolution of the 3D images. In a following step, as shown in FIG. 5A for two acquisition angles, the distance of the liver dome with respect to the top edge of the FOV (the vertical two-way arrows) was manually measured for both 3D images and 2D projection independently. Specifically, the pixel index of the liver dome was recorded using the MATLAB function "ginput". The distance was then calculated by multiplying the number of pixels from the liver dome to the top edge of the FOV with the reconstructed or interpolated voxel size along the head-to-foot direction. For measurement in the 3D images, the distance was calculated in the coronal plane and a central slice that best represents the liver dome was used for the analysis. Since the liver dome cannot be visualized clearly in certain acquisition angles, such as those shown in FIG. 5B, the distance was only measured in selected angles (0°-45°, 135°-225°, and 315°-360°), resulting in a total of 48 3D images for the comparison in each case. The analysis of the online-generated 3D images and real-time 2D projections was separated by approximately two months to ensure independent assessment. The distances measured from the 3D images and the 2D projections were compared using linear correlation.

The average reconstruction time to generate the offline database of motion states was 73.82±7.10 minutes. The imaging latency for the online matching step, averaged over all the datasets, was 329.9±3.1 ms, including the acquisition of online motion signature (178 ms) and the matching process (151.9±3.1 ms). FIG. 6 compares online-generated 3D liver images in two different motion states (right two columns, generated using the online matching algorithm) with corresponding real-time x-z projections (left column, generated from online signature data) for one patient dataset. FIG. 7 shows the same comparison in another patient dataset, which also suggests that the motion displacement in the online-generated 3D images matches well with that in the real-time 2D projections. Suspected lesions of this patient, as indicated by the arrows, can be clearly visualized in the 3D images in both coronal and sagittal planes. The 2D x-z projections serve as online motion signature data and can be used to validate the motion pattern in the corresponding 3D high-resolution images. The average distance of the liver dome to the top edge of the FOV was 24.55±0.52 mm and 23.46±9.99 mm for the real-time 2D projections and online-generated 3D images, respectively. A corresponding linear correlation plot is shown in FIG. 8, with a slope of 0.92 and an intercept of 1.26 mm. An R-square of 0.948 was obtained, indicating excellent correlations of the motion displacement of the liver dome in the two types of images and thus validating the accuracy of the disclosed motion-tracking approach.

In various implementations, an application of the disclosed motion tracking approach may be targeted to real-time adaptive radiation treatment using an MR-Linac system, where there would typically be an initial beam-off period for tumor contouring, dose calculation and other calibrations before the actual treatment. This period can be used for offline learning of the database 122 of motion states and signatures without prolonging the overall procedure or treatment. In some implementations, once the offline module 114 completes the offline learning process, computing device 110 may be able to track volumetric motion with a latency of about 300 ms, or less with additional optimization, to adapt the treatment in real-time. Such an adaptive radiation treatment can lead to dose escalation in the tumor and potential reduction in the number of treatment fractions for potentially improving overall therapeutic effects.

In various versions, computing device 110 can be applied to separate MRI simulation and Linac treatment using the concept of scannerless real-time imaging. Specifically, an external device, such as a motion sensor 160, can be used as the motion signature during both treatment planning (with MRI) and actual treatment (with Linac). In this scenario, although MR images are not directly acquired during treatment, motion signatures from the external device can still be monitored in real time, and thus pre-learned motion-resolved MR images can be used for real-time treatment adaptation using the disclosed motion tracking approach.

In various embodiments, golden-angle sampling scheme allows the computing device 110 to perform a simple continuous data acquisition during offline learning, so that a sufficient amount of data can be gathered efficiently. XD-GRASP reconstruction uses compressed sensing to reduce the amount of data, and thus the acquisition time, to learn offline motion states. Although a stack-of-stars acquisition has been described, computing device 110 may utilize other golden-angle sampling schemes, such as golden-angle Cartesian or 3D golden-angle radial sampling. Compared to stack-of-stars sampling, 3D radial sampling with a "kooshball" geometry may be a well-suited trajectory in certain implementations, where isotropic volumetric coverage is inherently acquired to extract isotropic 3D motion information without the need of interpolation. In addition to extracting motion signatures from acquired data itself, computing device 110 can be configured to insert additional navigator data explicitly in 3D golden-angle radial k-space sampling to serve as motion signatures. In various implementations, extending the disclosed motion tacking approach to a self-navigated 3D golden-angle phyllotaxis sampling strategy can improve the accuracy of treatment delivery. In addition, and perhaps more importantly, latency may be further reduced with the self-navigated 3D golden-angle trajectory, where the online matching step can be simplified with acquisitions of navigators or signatures only (e.g., a 1D k-space measurement orientated along the head-to-foot direction).

In various experiments, validation was performed using manually measured displacements in the x-z profiles acquired in real-time, which also serve as data to obtain online motion signatures. These measurements showed well correlations with the displacements in the pre-learned motion states and thus indicated that the motion tracking approach can effectively track motion in real time. Stack-of-stars sampling led to lower slice resolution, and interpolation was used to create 3D images with pseudo-isotropic voxel size. This can be addressed using a 3D golden-angle radial sampling scheme, as described above, at the expense of prolonging data acquisitions in the offline learning step. Code optimization, using for example C++ or python, can increase matching speed by the online module 116 and the overall latency may be further reduced to about 200 ms or less for improved real-time beam adaptation in an MR-Linac system 130. The temporal resolution and/or number of motion states of the 4D motion-resolved images, together with the spatial resolution, can be further increased by having the offline module 114 acquire more spokes at the cost of increased scan time for the offline learning step, so that a large number of motion states can be reconstructed.

Accurate and precise treatment delivery is highly desired in radiation therapy to maximize irradiation in a tumor and to minimize toxicity in healthy tissue surrounding the tumor. The use of MRI to guide radiation therapy has gained substantial interest in recent years due to its superior soft-tissue contrast, absence of ionizing radiation, and increased flexibility to acquire multi-parametric images that can be used both for pre-treatment planning and for post-treatment evaluation. The MR-Linac system, combining an MRI scanner and a linear accelerator, is available for simultaneous imaging and adaptive radiation-treatment (e.g., MR-guidance during treatment), which may particularly be useful for body applications. However, one of the major challenges associated with MRI-guided radiation therapy is the relatively slow imaging speed of MRI for capturing volumetric motion in real time. Indeed, even with the latest MRI acquisition and reconstruction technologies, high-resolution real-time MRI is still limited to 2D acquisitions, which often suffer from through-plane motion misregistration and suboptimal interpretation of motion. In embodiments described herein, "real-time" is defined as low imaging latency with respect to organ motion, including acquisition time and reconstruction time. For example, having a latency below ~200-300 ms can be considered real time for characterizing motion in most human organs. As a result, moving organs, such as the lung and the liver, pose a significant challenge for MRI-guided adaptive treatment delivery.

Example embodiments of a motion tracking approach, which pre-learns motion states in an offline step and then efficiently estimate 4D images from fast online signatures, has been described for real-time volumetric motion tracking. Compared to conventional rapid 4D MRI approaches, the disclosed approach shifts time-consuming data acquisition and image reconstruction work to the offline learning step and leaves simple operations for the online matching step, which dramatically reduces the latency for real-time tracking capabilities. Embodiments of the disclosure described herein can be directly applied to, for example, MR-Linac for adaptive radiation treatment, in example applications.

Various operations described herein can be implemented on computer systems, which can be of generally conventional design. FIG. 9 shows a simplified block diagram of a representative server system 900 (e.g., computing device 110) and client computer system 914 (e.g., computing device 110, condition detection system 130, condition detection system 130, imaging system 140, emitting system 150, and/or motion sensor 160) usable to implement certain embodiments of the present disclosure. In various embodiments, server system 900 or similar systems can implement services or servers described herein or portions thereof. Client computer system 914 or similar systems can implement clients described herein.

Server system 900 can have a modular design that incorporates a number of modules 902 (e.g., blades in a blade server embodiment); while two modules 902 are shown, any number can be provided. Each module 902 can include processing unit(s) 904 and local storage 906.

Processing unit(s) 904 can include a single processor, which can have one or more cores, or multiple processors. In some embodiments, processing unit(s) 904 can include a general-purpose primary processor as well as one or more special-purpose co-processors such as graphics processors, digital signal processors, or the like. In some embodiments, some or all processing units 904 can be implemented using customized circuits, such as application specific integrated circuits (ASICs) or field programmable gate arrays (FPGAs). In some embodiments, such integrated circuits execute instructions that are stored on the circuit itself. In other embodiments, processing unit(s) 904 can execute instructions stored in local storage 906. Any type of processors in any combination can be included in processing unit(s) 904.

Local storage 906 can include volatile storage media (e.g., conventional DRAM, SRAM, SDRAM, or the like) and/or non-volatile storage media (e.g., magnetic or optical disk, flash memory, or the like). Storage media incorporated in local storage 906 can be fixed, removable or upgradeable as desired. Local storage 906 can be physically or logically divided into various subunits such as a system memory, a read-only memory (ROM), and a permanent storage device. The system memory can be a read-and-write memory device or a volatile read-and-write memory, such as dynamic random-access memory. The system memory can store some or all of the instructions and data that processing unit(s) 904 need at runtime. The ROM can store static data and instructions that are needed by processing unit(s) 904. The permanent storage device can be a non-volatile read-and-write memory device that can store instructions and data even when module 902 is powered down. The term "storage medium" as used herein includes any medium in which data can be stored indefinitely (subject to overwriting, electrical disturbance, power loss, or the like) and does not include carrier waves and transitory electronic signals propagating wirelessly or over wired connections.

In some embodiments, local storage 906 can store one or more software programs to be executed by processing unit(s) 904, such as an operating system and/or programs implementing various server functions such as functions of the data processing system 9300 of FIG. 2, the node graph generation system 90, or any other system described herein, or any other server(s) associated with data processing system 9300 of FIG. 2 or the node graph generation system 90 or any other system described herein.

"Software" refers generally to sequences of instructions that, when executed by processing unit(s) 904 cause server system 900 (or portions thereof) to perform various operations, thus defining one or more specific machine embodiments that execute and perform the operations of the software programs. The instructions can be stored as firmware residing in read-only memory and/or program code stored in non-volatile storage media that can be read into volatile working memory for execution by processing unit(s) 904. Software can be implemented as a single program or a collection of separate programs or program modules that interact as desired. From local storage 906 (or non-local storage described below), processing unit(s) 904 can retrieve program instructions to execute and data to process in order to execute various operations described above.

In some server systems 900, multiple modules 902 can be interconnected via a bus or other interconnect 908, forming a local area network that supports communication between modules 902 and other components of server system 900. Interconnect 908 can be implemented using various technologies including server racks, hubs, routers, etc.

A wide area network (WAN) interface 910 can provide data communication capability between the local area network (interconnect 908) and a larger network, such as the Internet. Conventional or other activities technologies can be used, including wired (e.g., Ethernet, IEEE 802.3 standards) and/or wireless technologies (e.g., Wi-Fi, IEEE 802.11 standards).

In some embodiments, local storage 906 is intended to provide working memory for processing unit(s) 904, providing fast access to programs and/or data to be processed while reducing traffic on interconnect 908. Storage for larger quantities of data can be provided on the local area network by one or more mass storage subsystems 912 that can be connected to interconnect 908. Mass storage subsystem 912 can be based on magnetic, optical, semiconductor, or other data storage media. Direct attached storage, storage area networks, network-attached storage, and the like can be used. Any data stores or other collections of data described herein as being produced, consumed, or maintained by a service or server can be stored in mass storage subsystem 912. In some embodiments, additional data storage resources may be accessible via WAN interface 910 (potentially with increased latency).

Server system 900 can operate in response to requests received via WAN interface 910. For example, one of modules 902 can implement a supervisory function and assign discrete tasks to other modules 902 in response to received requests. Conventional work allocation techniques can be used. As requests are processed, results can be returned to the requester via WAN interface 910. Such operation can generally be automated. Further, in some embodiments, WAN interface 910 can connect multiple server systems 900 to each other, providing scalable systems capable of managing high volumes of activity. Conventional or other techniques for managing server systems and server farms (collections of server systems that cooperate) can be used, including dynamic resource allocation and reallocation.

Server system 900 can interact with various user-owned or user-operated devices via a wide-area network such as the Internet. An example of a user-operated device is shown in FIG. 9 as client computing system 914. Client computing system 914 can be implemented, for example, as a consumer device such as a smartphone, other mobile phone, tablet computer, wearable computing device (e.g., smart watch, eyeglasses), desktop computer, laptop computer, and so on.

example, client computing system 914 can communicate via WAN interface 910. Client computing system 914 can include conventional computer components such as processing unit(s) 916, storage device 918, network interface 920, user input device 922, and user output device 924. Client computing system 914 can be a computing device implemented in a variety of form factors, such as a desktop computer, laptop computer, tablet computer, smartphone, other mobile computing device, wearable computing device, or the like.

Processor 916 and storage device 918 can be similar to processing unit(s) 904 and local storage 906 described above. Suitable devices can be selected based on the demands to be placed on client computing system 914; for example, client computing system 914 can be implemented as a "thin" client with limited processing capability or as a high-powered computing device. Client computing system 914 can be provisioned with program code executable by processing unit(s) 916 to enable various interactions with server system 900 of a message management service such as accessing messages, performing actions on messages, and other interactions described above. Some client computing systems 914 can also interact with a messaging service independently of the message management service.

Network interface 920 can provide a connection to a wide area network (e.g., the Internet) to which WAN interface 910 of server system 900 is also connected. In various embodiments, network interface 920 can include a wired interface (e.g., Ethernet) and/or a wireless interface implementing various RF data communication standards such as Wi-Fi, Bluetooth, or cellular data network standards (e.g., 3G, 4G, LTE, etc.).

User input device 922 can include any device (or devices) via which a user can provide signals to client computing system 914; client computing system 914 can interpret the signals as indicative of particular user requests or information. In various embodiments, user input device 922 can include any or all of a keyboard, touch pad, touch screen, mouse or other pointing device, scroll wheel, click wheel, dial, button, switch, keypad, microphone, and so on.

User output device 924 can include any device via which client computing system 914 can provide information to a user. For example, user output device 924 can include a display to display images generated by or delivered to client computing system 914. The display can incorporate various image generation technologies, e.g., a liquid crystal display (LCD), light-emitting diode (LED) including organic light-emitting diodes (OLED), projection system, cathode ray tube (CRT), or the like, together with supporting electronics (e.g., digital-to-analog or analog-to-digital converters, signal processors, or the like). Some embodiments can include a device such as a touchscreen that function as both input and output device. In some embodiments, other user output devices 924 can be provided in addition to or instead of a display. Examples include indicator lights, speakers, tactile "display" devices, printers, and so on.

Some embodiments include electronic components, such as microprocessors, storage and memory that store computer program instructions in a computer readable storage medium. Many of the features described in this specification can be implemented as processes that are specified as a set of program instructions encoded on a computer readable storage medium. When these program instructions are executed by one or more processing units, they cause the processing unit(s) to perform various operation indicated in the program instructions. Examples of program instructions or computer code include machine code, such as is produced by a compiler, and files including higher-level code that are executed by a computer, an electronic component, or a microprocessor using an interpreter. Through suitable programming, processing unit(s) 904 and 916 can provide various functionality for server system 900 and client computing system 914, including any of the functionality described herein as being performed by a server or client, or other functionality associated with message management services.

It will be appreciated that server system 900 and client computing system 914 are illustrative and that variations and modifications are possible. Computer systems used in connection with embodiments of the present disclosure can have other capabilities not specifically described here. Further, while server system 900 and client computing system 914 are described with reference to particular blocks, it is to be understood that these blocks are defined for convenience of description and are not intended to imply a particular physical arrangement of component parts. For instance, different blocks can be but need not be located in the same facility, in the same server rack, or on the same motherboard. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Embodiments of the present disclosure can be realized in a variety of apparatus including electronic devices implemented using any combination of circuitry and software.

Referring to FIG. 10, an example motion-tracking process 1000 is illustrated, according to various potential embodiments. Process 1000 may be implemented by or via computing device 110. Process 1000 may begin (1005) with offline signature generation (offline learning), which may be implemented by or via offline module 114, if a suitable set of motion signatures is not already available (e.g., in database 122), or if additional signatures are to be generated or added to database 122. Alternatively, process 1000 may begin with adaptive radiotherapy or online signature correlation ("matching"), which may be implemented by or via online module 116, if a suitable set of offline signatures is available. In various embodiments, process 1000 may comprise both offline learning (e.g., steps 1010-1025) followed by online matching (e.g., steps 1050-1070).

At 1010, images of a subject (e.g., a subject on platform 190) may be acquired (e.g., via, imaging system 140) to capture or represent movements (or potential movements) of subjects. Step 1010 acquires movements prior to radiotherapy, as similar movements may occur during radiotherapy. Imaging may occur for a certain time (e.g., 30 seconds, 1 minute, 2 minutes, 5 minutes, etc.) and/or for a certain number of motion cycles (e.g., 10 breathing cycles, 20 breathing cycles, 50 breathing cycles, 100 breathing cycles, 10 heartbeats, 50 heartbeats, 100 heartbeats, etc.). Movements that are captured may be autonomic, somatic, or otherwise (e.g., movements may have external causes, such as movements resulting from components of system 100 or otherwise). For example, controller 112 of computing device 110 may use imaging system 140 to perform imaging that captures potential movements.

At 1015, various motion states may be defined (e.g., by or via offline module 114). Motions states may comprise or represent, for example, certain phases or portions of various motions, such as certain frames or subsections of observed cycles (see, e.g., FIG. 4A). At 2010, a unique offline motion signature may be generated (e.g., by or via signature generator 115) to correspond to each motion state. At 1025, the motion states and offline motion signatures may be stored (e.g., in database 122) for subsequent use. Process 1000 may end (1090), or proceed to step 1050 for use during adaptive radiotherapy.

At 1050, one or more images may be acquired (e.g., using an MRI scanner of imaging system 140 in response to control signals from computing device 110). At 1055, the one or more images may be used to generate an online motion signature (e.g., by or via online module 116). The online motion signature may be generated without the relatively computationally-intense image reconstruction that may be performed during online signature generation. At 1060, the online signature may be compared with the set of offline motion signatures generated at 1020 to identify the offline motion signature that is most closely correlated with or matching the online motion signature generated at 1055. At 1065, a 3D motion state corresponding to the identified offline motion signature may be selected based on the comparison and correlation ("matching") at 1060.

Using the selected motion state, at 1070 various components (e.g., of system 100) may be adjusted to adapt the radiotherapy to the motion to thereby reduce toxicity to healthy tissue. For example, controller 112 of computing device 110 may send control signals to emitting system 150 to adjust the aim (e.g., location of the beam path), intensity, timing, shape, and/or other characteristics of the radiation beam(s) being used to deliver radiation to target(s). In various embodiments, a beam delivering radiotherapy may be realigned, reduced and increased in intensity, turned off and on (e.g., paused), or otherwise modified in real time to reduce, minimize, or avoid radiation reaching healthy tissue, and proportionally increase or maximize radiation reaching intended targets. Additionally or alternatively, the subject may be moved to position and reposition the target to increase or maximize radiation reaching the target and reduce or minimize radiation reaching surrounding tissue. For example, controller 112 may send control signals to a motorized platform 190 to make micro-adjustments to the position of the subject as deemed suitable. Process 1000 may return to step 1050 so as to continue tracking the target's movements and make subsequent adjustments to continue adapting the radiotherapy to subsequent motion.

In some embodiments, a selected motion state may be deemed to indicate what motions can be expected (i.e., are highly likely based on offline learning) for a certain time into the future (e.g., for a second or fraction thereof, or for more than one second, or for the remainder of a motion cycle, or for multiple motion cycles). To reduce computational and other demands on system 100, subsequent image acquisition at 1050 may be delayed to variable degrees following adjustments at 1070. For example, a motion state indicative of a bump to platform 190, muscle jerk, or abnormal breath (e.g., a deep breath) may be deemed to be less predictable (and thereby warrant closer monitoring) than a motion state corresponding with regular breathing. Consequently, certain motion states may indicate that a next cycle of signature matching may need to occur relatively sooner to account for the less predictable motion, relative to motion states that correspond to more predictable (more "normal") motion.

While the disclosure has been described with respect to specific embodiments, one skilled in the art will recognize that numerous modifications are possible. For instance, although specific examples of rules (including triggering conditions and/or resulting actions) and processes for generating suggested rules are described, other rules and processes can be implemented. Embodiments of the disclosure can be realized using a variety of computer systems and communication technologies including but not limited to specific examples described herein.

Embodiments of the present disclosure can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features of the present disclosure may be encoded and stored on various computer readable storage media; suitable media include magnetic disk or tape, optical storage media such as compact disk (CD) or DVD (digital versatile disk), flash memory, and other non-transitory media. Computer readable media encoded with the program code may be packaged with a compatible electronic device, or the program code may be provided separately from electronic devices (e.g., via Internet download or as a separately packaged computer-readable storage medium).

Thus, although the disclosure has been described with respect to specific embodiments, it will be appreciated that the disclosure is intended to cover all modifications and equivalents within the scope of the following claims.

Additional background, supporting information, and enabling disclosure can be found in the following references, incorporated herein by reference:

Cervino L, Du J, Jiang S B. MRI-guided tumor tracking in lung cancer radiotherapy. Phys Med Biol. 2011; 56:3773-3785.

Lagendijk J J, Raaymakers B W, Van den Berg C A, Moerland M A, Philippens M E, van Vulpen M. M R guidance in radiotherapy. Phys Med Biol 2014; 59(21): R349-369.

Raaymakers B W, Lagendijk J J, Overweg J, Kok J G, Raaijmakers A J, Kerkhof E M, van der Put R W, Meijsing I, Crijns S P, Benedosso F, van Vulpen M, de Graaff C H, Allen J, Brown K J. Integrating a 1.5 T MRI scanner with a 6 M V accelerator: proof of concept. Phys Med Biol 2009; 54(12):N229-237.

Dempsey J, Benoit D, Fitzsimmons J, Haghighat A, Li J, Low D, Mutic S, Palta J, Romeijn H and Sjoden G. A device for realtime 3D image-guided IMRT. Int J Radiat Oncol Biol Phys. 2005; 63(1):S202.

Keall P J, Mageras G S, Balter J M, Emery R S, Forster K M, Jiang S B, Kapatoes J M, Low D A, Murphy M J, Murray B R, Ramsey C R, Van Herk M B, Vedam S S, Wong J W, Yorke E. The management of respiratory motion in radiation oncology report of AAPM Task Group 76. Med Phys 4 2006; 33(10):3874-3900.

Bjerre T, Crijns S, Rosenschold P, Aznar M, Specht L, Larsen R, Keall P. Three-dimensional MRI-linac intra-fraction guidance using multiple orthogonal cine-MRI planes. Phys Med Biol. 2013; 58: 4943-4950.

Feng L, Srichai M B, Lim R P, Harrison A, King W, Adluru G, Dibella E V, Sodickson D K, Otazo R, Kim D. Highly accelerated real-time cardiac cine MRI using k-t SPARSE-SENSE. Magn Reson Med. 2013; 70(1):64-74

Chandarana H, Wang H, Tijssen R H N, Das I J. Emerging role of MRI in radiation therapy. Journal of magnetic resonance imaging: JMRI 2018; 48(6):1468-1478.

Tyagi N, Fontenla S, Zelefsky M, Chong-Ton M, Ostergren K, Shah N, Warner L, Kadbi M, Mechalakos J, Hunt M. Clinical workflow for MR-only simulation and planning in prostate. Radiat Oncol 2017; 12(1):119.

Kerkmeijer L G W, Maspero M, Meijer G J, van der Voort van Zyp J R N, de Boer H C J, van den Berg C A T. Magnetic Resonance Imaging only Workflow for Radiotherapy Simulation and Planning in Prostate Cancer. Clin Oncol (R Coll Radiol) 2018; 30(11):692-701.

Raaymakers B W, Jurgenliemk-Schulz I M, Bol G H, Glitzner M, Kotte A, van Asselen B, de Boer J C J, Bluemink J J, Hackett S L, Moerland M A, Woodings S J, Wolthaus J W H, van Zijp H M, Philippens M E P, Tijssen R, Kok J G M, de Groot-van Breugel E N, Kiekebosch I, Meijers L T C, Nomden C N, Sikkes G G, Doornaert P A H, Eppinga W S C, Kasperts N, Kerkmeijer L G W, Tersteeg J H A, Brown K J, Pais B, Woodhead P, Lagendijk J J W. First patients treated with a 1.5 T MRI-Linac: clinical proof of concept of a high-precision, high-field MRI guided radiotherapy treatment. Phys Med Biol 2017; 62(23):L41-L50.

Bjerre T, Crijns S, af Rosenschold P M, Aznar M, Specht L, Larsen R, Keall P. Three-dimensional MRI-linac intra-fraction guidance using multiple orthogonal cine-MRI planes. Phys Med Biol 2013; 58(14):4943-4950.

Paganelli C, Lee D, Kipritidis J, Whelan B, Greer P B, Baroni G, Riboldi M, Keall P. Feasibility study on 3D image reconstruction from 2D orthogonal cine-MRI for MRI-guided radiotherapy. J Med Imaging Radiat Oncol 2018; 62(3):389-400.

Zhang Q, Pevsner A, Hertanto A, Hu Y C, Rosenzweig K E, Ling C C, Mageras G S. A patient-specific respiratory model of anatomical motion for radiation treatment planning. Med Phys 2007; 34(12):4772-4781.

Li R, Lewis J H, Jia X, Zhao T, Liu W, Wuenschel S, Lamb J, Yang D, Low D A, Jiang S B. On a PCA-based lung motion model. Phys Med Biol 162011; 56(18):6009-6030.

Fayad H, Pan T, Pradier O, Visvikis D. Patient specific respiratory motion modeling using a 3D patient's external surface. Med Phys 2012; 39(6):3386-3395.

Stemkens B, Tijssen R H, de Senneville B D, Lagendijk J J, van den Berg C A. Image-driven, model-based 3D abdominal motion estimation for M R-guided radiotherapy. Phys Med Biol 2016; 61(14):5335-5355.

Han F, Zhou Z, Du D, Gao Y, Rashid S, Cao M, Shaverdian N, Hegde J V, Steinberg M, Lee P, Raldow A, Low D A, Sheng K, Yang Y, Hu P. Respiratory motion-resolved, self-gated 4D-MRI using Rotating Cartesian K-space (ROCK): Initial clinical experience on an MRI-guided radiotherapy system. Radiother Oncol 2018; 127(3):467-473.

Stemkens B, Paulson E S, Tijssen R H N. Nuts and bolts of 4D-MRI for radiotherapy. Phys Med Biol 2018; 63(21): 21TR01.

Deng Z, Pang J, Yang W, Yue Y, Sharif B, Tuli R, Li D, Fraass B, Fan Z. Four-dimensional MRI using three-dimensional radial sampling with respiratory self-gating to characterize temporal phase-resolved respiratory motion in the abdomen. Magnetic resonance in medicine 2016; 75(4):1574-1585.

Winkelmann S, Schaeffter T, Koehler T, Eggers H, Doessel O. An optimal radial profile order based on the Golden Ratio for time-resolved MRI. IEEE Trans Med Imaging 2007; 26(1):68-76.

Feng L, Axel L, Chandarana H, Block K T, Sodickson D K, Otazo R. X D-GRASP: Golden-angle radial MRI with reconstruction of extra motion-state dimensions using compressed sensing. Magn Reason Med 2016; 75(2):775-788.

Feng L, Grimm R, Block K T, Chandarana H, Kim S, Xu J, Axel L, Sodickson D K, Otazo R. Golden-angle radial sparse parallel MRI: combination of compressed sensing, parallel imaging, and golden-angle radial sampling for fast and flexible dynamic volumetric MRI. Magn Reson Med 2014; 72(3):707-717.

Feng L, Huang C, Shanbhogue K, Sodickson D K, Chandarana H, Otazo R. RACER-GRASP: Respiratory-weighted, aortic contrast enhancement-guided and coil-unstreaking golden-angle radial sparse MRI. Magnetic resonance in medicine 2018; 80(1):77-89.

Chandarana H, Block T K, Rosenkrantz A B, Lim R P, Kim D, Mossa D J, Babb J S, Kiefer B, Lee V S. Free-breathing radial 3D fat-suppressed T1-weighted gradient echo sequence: a viable alternative for contrast-enhanced liver imaging in patients unable to suspend respiration. Investigative radiology 2011; 46(10):648-653.

Walsh D O, Gmitro A F, Marcellin M W. Adaptive reconstruction of phased array MR imagery. Magnetic resonance in medicine 2000; 43(5):682-690.

Preiswerk F, Toews M, Cheng C C, Chiou J G, Mei C S, Schaefer L F, Hoge W S, Schwartz B M, Panych L P, Madore B. Hybrid MRI-Ultrasound acquisitions, and scannerless real-time imaging. Magn Reson Med 2017; 78(3):897-908.

Cheng J Y, Zhang T, Ruangwattanapaisarn N, Alley M T, Uecker M, Pauly J M, Lustig M, Vasanawala S S. Free-breathing pediatric MRI with nonrigid motion correction and acceleration. Journal of magnetic resonance imaging: JMRI 2015; 42(2):407-420.

Piccini D, Littmann A, Nielles-Vallespin S, Zenge M O. Respiratory self-navigation for whole-heart bright-blood coronary MRI: methods for robust isolation and automatic segmentation of the blood pool. Magn Reson Med 2012; 68(2):571-579.

Chan R W, Ramsay E A, Cunningham C H, Plewes D B. Temporal Stability of Adaptive 3D Radial MRI Using Multidimensional Golden Means. Magnetic Resonance in Medicine 2009; 61(2):354-363.

Stehning C, Bornert P, Nehrke K, Eggers H, Stuber M. Free-breathing whole-heart coronary MRA with 3D radial SSFP and self-navigated image reconstruction. Magn Reson Med 2005; 54(2):476-480.

Pang J, Sharif B, Fan Z, Bi X, Arsanjani R, Berman D S, Li D. ECG and navigator-free four-dimensional whole-heart coronary MRA for simultaneous visualization of cardiac anatomy and function. Magn Reson Med 2014; 72(5):1208-1217.

Piccini D, Littmann A, Nielles-Vallespin S, Zenge M O. Spiral phyllotaxis: the natural way to construct a 3D radial trajectory in MRI. Magnetic resonance in medicine 2011; 66(4):1049-1056.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the terms "exemplary," "example," "potential," and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the Figures. It should be noted that the orientation of various elements may differ according to other exemplary embodiments, and that such variations are intended to be encompassed by the present disclosure.

The embodiments described herein have been described with reference to drawings. The drawings illustrate certain details of specific embodiments that implement the systems, methods and programs described herein. However, describing the embodiments with drawings should not be construed as imposing on the disclosure any limitations that may be present in the drawings.

While various inventive embodiments have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive embodiments described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of

What is claimed is:

1. A magnetic resonance imaging (MM) method for tracking 3D organ motion using high spatial resolution 3D motion states and high temporal resolution motion signature data, the method comprising:
 performing, by one or more processors, offline learning comprising generating pairs of 3D motion states and offline motion signatures based on MM images acquired during one or more motion cycles;
 generating, by the one or more processors, an online motion signature without image reconstruction; and
 performing, by the one or more processors, online signature matching comprising comparing the online motion signature with offline motion signatures to identify a corresponding 3D motion state so as to account for motion during radiotherapy by adapting delivery of radiation according to target position and/or target shape and thereby improve treatment accuracy to reduce toxicity to healthy tissue surrounding a target of the radiotherapy.

2. The MM method of claim 1, further comprising administering a radiotherapy to a subject, wherein offline learning is performed before commencement of the radiotherapy, and wherein online matching is performed during the radiotherapy.

3. The Mill method of claim 1, wherein offline learning comprises reconstructing one 3D image for each motion state from data acquired continuously over multiple motion cycles generating a unique motion signature representing each motion state.

4. The Mill method of claim 1, wherein offline learning comprises using a golden-angle stack-of-stars k-space sampling scheme, wherein in-plane k-space dimensions $k_x$ and $k_y$ are sampled using a radial trajectory, and the through-plane k-space dimension $k_z$, is sampled using a Cartesian trajectory.

5. The MRI method of claim 1, wherein motion signatures are directly extracted from the acquired data for each motion state using all of a central k-space to form projections along time across the organ of interest, wherein at the central k-space, a difference between $k_x$ and $k_y$ is zero.

6. The MRI method of claim 1, wherein a 3D golden-angle radial sampling trajectory with kooshball geometry is used during offline learning.

7. The MRI method of claim 1, wherein offline learning comprises explicitly inserting at least one of a 1D navigator, a 2D navigator, and a low-resolution 3D navigator as motion signature.

8. The MRI method of claim 1, wherein offline learning comprises using a 3D golden-angle Cartesian trajectory, wherein two-dimensional phase-encoding in a $k_y$-$k_z$, plane is segmented into different interleaves, wherein each interleave is rotated by the golden angle.

9. The MRI method of claim 1, wherein 3D motion states are reconstructed using a compressed sensing reconstruction, in which a sparsity constraint is enforced to exploit correlations along a motion dimension.

10. The MRI method of claim 1, further comprising building a database of the pairs of motion states and motion signatures learned offline.

11. The MRI method of claim 1, wherein online matching comprises performing signature-only acquisitions, and selecting a motion state with a signature correlated with acquired data corresponding to real-time 3D motion tracking.

12. The MRI method of claim 1, wherein the online matching is performed while applying radiotherapy to a subject.

13. A computer-implemented method of performing adaptive radiotherapy, the method comprising:
- detecting, by a computing device using an imaging system, a motion signature of a subject with latency less than 0.2 seconds;
- identifying, by the computing device, a predetermined motion signature with which the detected motion signature is correlated;
- selecting the predetermined 3D motion state that corresponds to the identified predetermined motion signature; and
- adapting, by the computing device, the radiotherapy based on the selected 3D motion state to a new target location and/or shape so as to increase treatment accuracy and thereby reduce toxicity to healthy tissue.

14. The method of claim 13, wherein the imaging system includes an MM scanner.

15. The method of claim 13, wherein the radiotherapy is performed using at least a linear accelerator.

16. The method of 13, wherein the predetermined motion signature is learned, via an offline module of the computing device, through offline learning of pairs of motion states and motion signatures.

17. The method of 13, wherein the identifying the predetermined motion signature step is part of online matching, via an online module of the computing device, of high temporal resolution signature data with high spatial resolution 3D motion states.

18. A system for performing adaptive radiotherapy, the system comprising:
- an imaging system configured to detect a motion state of a subject;
- a therapeutic system configured to apply radiation to the subject; and
- a computing device configured to control the imaging system and the therapeutic system to perform radiotherapy on the subject, the computing device having one or more processors and a memory storing instructions that, when executed by the one or more processors, cause the one or more processors to:
  - detect, using the imaging system, a motion signature of the subject;
  - identify a predetermined motion signature with which the detected motion signature is correlated;
  - select a predetermined 3D motion state that corresponds to the identified predetermined motion signature; and
  - adapt the radiotherapy, via the therapeutic system, based on the selected 3D motion state so as to account for motion of the subject during radiotherapy and increase a proportion of radiation applied to a target relative to tissue surrounding the target.

19. The system of claim 18, wherein adapting the radiotherapy comprises adjusting a position of a radiation beam, a shape of a radiation beam, and/or a timing of a radiation beam.

20. The system of claim 18, wherein the radiotherapy is performed using at least a linear accelerator.

* * * * *